United States Patent
Niimori

(10) Patent No.: US 11,802,284 B2
(45) Date of Patent: Oct. 31, 2023

(54) MEDICINE FOR TREATING CANCER AND METHOD FOR TREATING CANCER

(71) Applicants: NATIONAL UNIVERSITY CORPORATION KUMAMOTO UNIVERSITY, Kumamoto (JP); TOKYO INSTITUTE OF TECHNOLOGY, Tokyo (JP)

(72) Inventor: Kanako Niimori, Kumamoto (JP)

(73) Assignees: NATIONAL UNIVERSITY CORPORATION KUMAMOTO UNIVERSITY, Kumamoto (JP); TOKYO INSTITUTE OF TECHNOLOGY, Kumamoto (JP)

( * ) Notice: Subject to any disclaimer, the term of this patent is extended or adjusted under 35 U.S.C. 154(b) by 572 days.

(21) Appl. No.: 16/918,520

(22) Filed: Jul. 1, 2020

(65) Prior Publication Data
US 2020/0339995 A1 Oct. 29, 2020

Related U.S. Application Data

(63) Continuation of application No. 15/739,617, filed as application No. PCT/JP2016/066393 on Jun. 2, 2016, now abandoned.

(30) Foreign Application Priority Data

Jun. 25, 2015 (JP) ................... 2015-128139

(51) Int. Cl.
| | |
|---|---|
| *A61K 48/00* | (2006.01) |
| *A61K 31/713* | (2006.01) |
| *A61P 35/00* | (2006.01) |
| *C12N 15/113* | (2010.01) |
| *A61K 45/00* | (2006.01) |
| *C07K 16/18* | (2006.01) |
| *C07K 16/30* | (2006.01) |
| *A61K 39/00* | (2006.01) |

(52) U.S. Cl.
CPC ........ *C12N 15/1135* (2013.01); *A61K 31/713* (2013.01); *A61K 45/00* (2013.01); *A61K 48/00* (2013.01); *A61P 35/00* (2018.01); *C07K 16/18* (2013.01); *C07K 16/30* (2013.01); *A61K 2039/505* (2013.01); *C12N 2310/14* (2013.01)

(58) Field of Classification Search
CPC .............. A61K 31/7088; A61K 31/711; A61K 31/713; A61K 31/712; A61K 31/7115; A61K 31/7125; A61K 2039/505; C07K 16/30

See application file for complete search history.

(56) References Cited

U.S. PATENT DOCUMENTS

2014/0026234 A1 1/2014 Sotgia

FOREIGN PATENT DOCUMENTS

| | | |
|---|---|---|
| JP | 2013061253 A2 | 4/2013 |
| WO | 2012103455 A1 | 8/2012 |

OTHER PUBLICATIONS

Robinson, PLOS Biology, 2004, vol. 1, pp. 0018-0020 (Year: 2004).*
Lau et al. (Science, 2006, vol. 313, pp. 363-367) (Year: 2006).*
Gunther et al. (European Journal of Pharmaceutical and Biopharmaceutics, 2011, vol. 77, pp. 438-449) (Year: 2011).*
Zhu et al. (PNAS, 2015, vol. 112, pp. 7779-7784) (Year: 2015).*
International Search Report dated Aug. 16, 2016 filed in PCT/JP2016/066393.
Nakayasu et al., Nuclear matrins: Identification of the major nuclear matrix proteins, Proc. Natl. Acad. Sci. U.S.A. 88, pp. 10312-10316, Nov. 1991, Cell Biology.; Cited in Specification.
Belgrader et al., Molecular Cloning of Matrin 3, The Journal of Biological Chemistry, vol. 266, No. 15, Issue of May 25, pp. 9893-9899, 1991 .; Cited in Specification.
Salton et al., Matrin 3 Binds and Stabilizes mRNA, PLoS One, vol. 6, Issue 8, e23882, Aug. 2011.; Cited in Specification.
Skowronska-Krawczyk et al., Required enhancer-matrin-3 network interactions for a homeodomain transcription program, Nature, vol. 514, pp. 257-261, Oct. 9, 2014.; Cited in Specification.
Johnson et al., Mutations in the Matrin 3 gene cause familial amyotrophic lateral sclerosis, Nature Neuroscience, vol. 17, No. 5, pp. 664-666, May 2014.; Cited in Specification.
Ulbright et al., Primitive neuroectodermal tumors in patients with testicular germ cell tumors usually resemble pediatric-type central nervous system embryonal neoplasms and lack chromosome 22 rearrangements, Modern Pathology, 2010, vol. 23, pp. 972-980, Abstract, Table 2.; Cited in ISR.

(Continued)

*Primary Examiner* — Karen A. Canella
(74) *Attorney, Agent, or Firm* — Rankin, Hill & Clark LLP

(57) ABSTRACT

An object of the present invention is to reveal a role of a stem cell control factor including Matrin-3 in cancer exhibiting neural differentiation including small cell lung cancer, and develop a medicine useful for treating cancer and the like based on the role. Among cancers having the cancer stem cell controlling mechanism, in cancer exhibiting the differentiation potency, the peculiar balance where both of expression of a stem cell maintenance factor and expression of a differentiation promoting factor are higher as compared with normal cells is retained. Additionally, in undifferentiated cancer, the peculiar balance where expression of a stem cell maintenance factor is higher as compared with normal cells is retained. In cancer in which the cancer stem cell controlling mechanism exists, these peculiar balances of a stem cell control factor different from the balance of normal cells exist. In the medicine for treating cancer and the method for treating cancer of the present invention, proliferativeness of cancer is suppressed by breaking down this balance of a stem cell control factor.

2 Claims, 26 Drawing Sheets

Specification includes a Sequence Listing.

(56) References Cited

OTHER PUBLICATIONS

Chen et al., hnRNP K expression and its clinical significance in human lung cancer tissues, Chin J Lung Cancer, 2008, vol. 11, No. 2, pp. 241-245, English abstract; Cited in ISR.

Sato et al., The expression of DNA methyltransferases and methyl-CpG-binding proteins is not associated with the methylation status of p14ARF, p16INK4a and RASSF1A in human lung cancer cell lines, Oncogene, 2002, vol. 21, pp. 4822-4829, Abstract.; Cited in ISR.

Owonikoko et al., Evaluating markers of cisplatin sensitivity and survival in small cell lung cancer, Cancer Research, 2014, vol. 74, No. 19, Supp. SUPPL. 1, Abstract No. 922.; Cited in ISR.

S. Lee et al.: "Aurora A is a Repressed Effector Target of the Chromatin Remodeling Protein INI1/hSNF5 Required for Rhabdoid Tumor Cell Survival", Cancer Research, Apr. 26, 2011, pp. 3225-3235, vol. 71, No. 9, American Association of Cancer Research, Philadelphia, PA.; Cited in European Extended Search Report.

H. Lin et al.: "Loss of SNF5 Expression Correlates with Poor Patient Survival in Melanoma", Clinical Cancer Research, Oct. 6, 2009, pp. 6404-6411, vol. 15, No. 20, American Association of Cancer Research, Philadelphia, PA.; Cited n EESR.

K.H. Kim et al.: "Mechanisms by which SMARCB1 loss drives rhabdoid tumor growth", Cancer Genetics, Sep. 1, 2014, pp. 365-372, vol. 207, No. 9, Elsevier Inc., Atlanta, GA.; Cited in EESR.

P. Subbarayalu et al.: "Abstract P4-05-09: Matrin 3: A novel microtubule associated RNA binding protein that acts as a potent tumor suppressor Cancer Research", May 15, 2015, pp. 1-4, American Association of Cancer Research, Philadelphia, PA.; Cited in EESR.

P. Przygodzka et al.: "Matrin 3 as a key regulator of endothelial cell survival", Experimental Cell Research, Dec. 13, 2010, pp. 802-811, vol. 317, No. 6, Elsevier Inc., Atlanta, GA.; Cited in EESR.

H. Kato et al.: "Knock down of hSNF5/Ini1 causes cell cycle arrest and apoptosis in a p53-dependent manner", Biochemical and Biophysical Research Communications, Sep. 28, 2007, pp. 580-585, vol. 361, No. 3, Elsevier Inc., Atlanta, GA.; Cited in EESR.

B. Goldenson et al.: "The aurora kinases in cell cycle and leukemia", Oncogene, Mar. 17, 2014, pp. 537-545, vol. 34, No. 5, Macmillan Publishers Limited, United Kingdom; Cited in EESR.

European Search Report dated Jan. 23, 2019 in the EP Patent Application No. 16814119.0.

Lorenzer et al (Journal of Controlled Release, 2015, vol. 203, pp. 1-15) (Year: 2015); Cited in US OA dated Mar. 5, 2020 issued for U.S. Appl. No. 15/739,617.

Merkel et al. (Advanced Drug Delivery Reviews, 2014, vol. 75, pp. 112-128) (Year: 2014); Cited in US OA dated Mar. 5, 2020 issued for U.S. Appl. No. 15/739,617.

Rao et al. (Advanced Drug Delivery Reviews, 2009, vol. 61, pp. 746-759) (Year: 2009); Cited in US OA dated Mar. 5, 2020 issued for U.S. Appl. No. 15/739,617.

Moore et al. ('Short Hairpin RNA (sh RNA): Design, Delivery, and Assessment of Gene Knockdown', In: RNA Therapeutics, M. Sioud, Ed., Methods in Molecular Biology, 2010, vol. 629, pp. 139-156) (Year: 2010); Cited in US OA dated Mar. 5, 2020 issued for U.S. Appl. No. 15/739,617.

Internet Archive, Santacruz Biotech, Captures Aug. 7, 2014 and Aug. 13, 2014 (Year: 2014); Cited in US OA dated Mar. 5, 2020 issued for U.S. Appl. No. 15/739,617.

Ee et al. (Cancer Research, 2011, vol. 71, pp. 3225-3235) (Year: 2011); Cited in US OA dated Mar. 5, 2020 issued for U.S. Appl. No. 15/739,617.

Belgrader et al (Journal of Biological Chemistry, 1991, vol. 266, pp. 9893-9899) (Year: 1991); Cited in US OA dated Mar. 5, 2020 issued for U.S. Appl. No. 15/739,617.

\* cited by examiner

FIG. 21
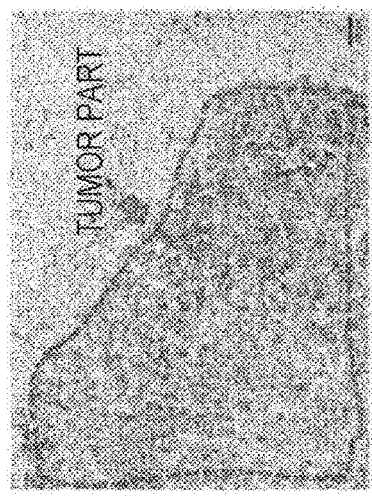
MERKEL'S CELL CANCER
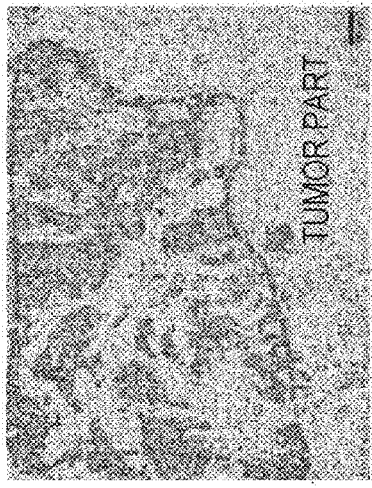
MERKEL'S CELL CANCER
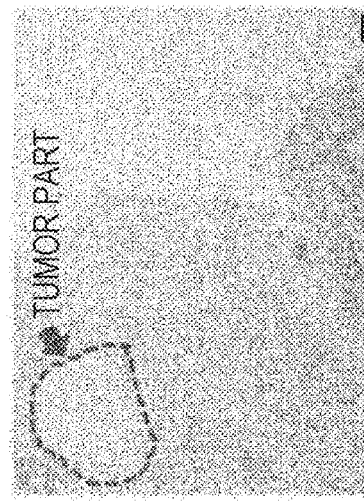
SCC (SQUAMOUS CELL CARCINOMA)
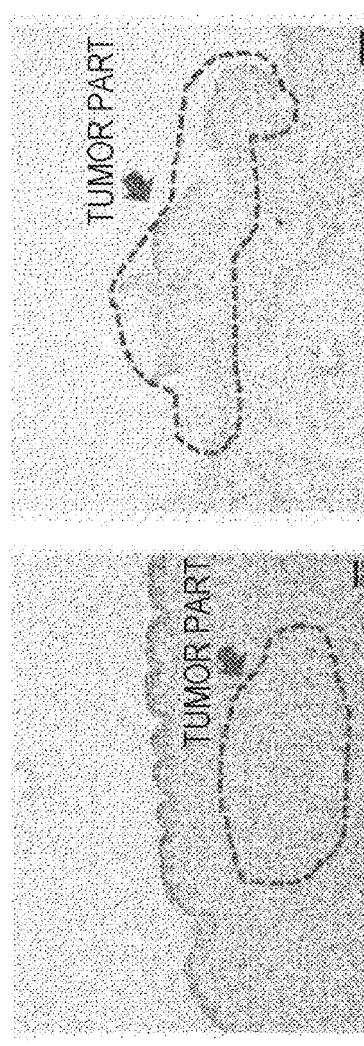
Paget's DISEASE (APOCRINE ADENOCARCINOMA)
NF1 (Neuro Fibroma 1)

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: sc-62605A sense

<400> SEQUENCE: 1
```

```
gcuacccagu cuuuaaguat t                                              21

<210> SEQ ID NO 2
<211> LENGTH: 21
<212> TYPE: DNA
<213> ORGANISM: Artificial Sequence
<220> FEATURE:
<223> OTHER INFORMATION: sc-62605A antisense

<400> SEQUENCE: 2
uacuuaaaga cugguagct t                                               21

<210> SEQ ID NO 3
<211> LENGTH: 21
<212> TYPE: DNA
<213> ORGANISM: Artificial Sequence
<220> FEATURE:
<223> OTHER INFORMATION: sc-62605B sense

<400> SEQUENCE: 3
cuaguacuuc uucccauaat t                                              21

<210> SEQ ID NO 4
<211> LENGTH: 21
<212> TYPE: DNA
<213> ORGANISM: Artificial Sequence
<220> FEATURE:
<223> OTHER INFORMATION: sc-62605B antisense

<400> SEQUENCE: 4
uuaugggaag aaguacuagt t                                              21

<210> SEQ ID NO 5
<211> LENGTH: 21
<212> TYPE: DNA
<213> ORGANISM: Artificial Sequence
<220> FEATURE:
<223> OTHER INFORMATION: sc-62605C sense

<400> SEQUENCE: 5
ccauuuggag ucauuucaat t                                              21

<210> SEQ ID NO 6
<211> LENGTH: 21
<212> TYPE: DNA
<213> ORGANISM: Artificial Sequence
<220> FEATURE:
<223> OTHER INFORMATION: sc-62605C antisense

<400> SEQUENCE: 6
uugaaaugac uccaaauggt t                                              21

<210> SEQ ID NO 7
<211> LENGTH: 29
<212> TYPE: DNA
<213> ORGANISM: Artificial Sequence
<220> FEATURE:
<223> OTHER INFORMATION: Matrin-3-shRNA1

<400> SEQUENCE: 7
tgagttcttc attgaatcaa caaggagct                                      29

<210> SEQ ID NO 8
<211> LENGTH: 29
<212> TYPE: DNA
```

```
<213> ORGANISM: Artificial Sequence
<220> FEATURE:
<223> OTHER INFORMATION: Matrin-3-shRNA2

<400> SEQUENCE: 8
tatccagagg acaagattac tcctgagaa                                29

<210> SEQ ID NO 9
<211> LENGTH: 29
<212> TYPE: DNA
<213> ORGANISM: Artificial Sequence
<220> FEATURE:
<223> OTHER INFORMATION: Matrin-3-shRNA3

<400> SEQUENCE: 9
gatttgccag ttcattctaa taaggagtg                                29

<210> SEQ ID NO 10
<211> LENGTH: 29
<212> TYPE: DNA
<213> ORGANISM: Artificial Sequence
<220> FEATURE:
<223> OTHER INFORMATION: Matrin-3-shRNA4

<400> SEQUENCE: 10
aagtatgcca gcatctcttg gaaggatga                                29

<210> SEQ ID NO 11
<211> LENGTH: 21
<212> TYPE: DNA
<213> ORGANISM: Artificial Sequence
<220> FEATURE:
<223> OTHER INFORMATION: sc-35670A sense

<400> SEQUENCE: 11
gcaaugacga aaguacaat t                                         21

<210> SEQ ID NO 12
<211> LENGTH: 21
<212> TYPE: DNA
<213> ORGANISM: Artificial Sequence
<220> FEATURE:
<223> OTHER INFORMATION: sc-35670A antisense

<400> SEQUENCE: 12
uuguacuucu cgucauugct t                                        21

<210> SEQ ID NO 13
<211> LENGTH: 21
<212> TYPE: DNA
<213> ORGANISM: Artificial Sequence
<220> FEATURE:
<223> OTHER INFORMATION: sc-35670B sense

<400> SEQUENCE: 13
ggaacaugaa ugagaagcut t                                        21

<210> SEQ ID NO 14
<211> LENGTH: 21
<212> TYPE: DNA
<213> ORGANISM: Artificial Sequence
<220> FEATURE:
<223> OTHER INFORMATION: sc-35670B antisense

<400> SEQUENCE: 14
agcuucucau ucauguucct t                                        21
```

```
<210> SEQ ID NO 15
<211> LENGTH: 21
<212> TYPE: DNA
<213> ORGANISM: Artificial Sequence
<220> FEATURE:
<223> OTHER INFORMATION: sc-35670C sense

<400> SEQUENCE: 15
ccacagacag cauccuagat t                                              21

<210> SEQ ID NO 16
<211> LENGTH: 21
<212> TYPE: DNA
<213> ORGANISM: Artificial Sequence
<220> FEATURE:
<223> OTHER INFORMATION: sc-35670C antisense

<400> SEQUENCE: 16
ucuaggaugc ugucuguggt t                                              21
```

MEDICINE FOR TREATING CANCER AND METHOD FOR TREATING CANCER

TECHNICAL FIELD

The present invention relates to a medicine for treating cancer and a method for treating cancer and the like. More particularly, the present invention relates to a medicine for treating cancer and a method for treating cancer and the like, based on the mechanism in which the stemness maintenance mechanism and the neural differentiation mechanism which exist in specific cancers such as small cell lung cancer are broken down by controlling expression or phosphorylation of a stem cell control factor such as Matrin-3, and consequently, proliferation of cancer is suppressed.

BACKGROUND ART

Small cell lung cancer is named so because it has the smaller cell size as compared with other cancers.

The characteristic of small cell lung cancer is that it progresses most rapidly among lung cancers, that is, it is poorly-differentiated and proliferates rapidly. For that reason, metastasis of small cell lung cancer to lymph nodes or other organs is seen from at an early stage of the cancer. And, in most cases, small cell lung cancer is found as the state of advanced cancer. Consequently, it is known that the lethality of small cell lung cancer is higher as compared with other cancers.

Currently, as treatment of small cell lung cancer, treatment with an anti-cancer agent or radiation is performed. These treatments contribute to prolongation of life expectancy. However, under the current situation, complete cure is extremely difficult. It is thought that if finding of small cell lung cancer at an early stage, suppression of growth of tumor, and suppression of metastasis become possible, the treatment outcome of small cell lung cancer is dramatically improved. However, regarding the molecular basis of small cell lung cancer, many points remain unsolved. For that reason, under the current situation, there is no effective treating method from which the high therapeutic effect can be expected.

Another well-known characteristic of small cell lung cancer having such characteristic is that the cancer exhibits neural differentiation.

Neural differentiation is phenomenon that stem cells differentiate into nervous cells by a stem cell maintenance factor. Although how this neural differentiation is controlled has been studied, it has not been revealed. Additionally, whether neural differentiation is involved in with the disease state of small cell lung cancer or not has not been revealed at all. Naturally, these studies have not led to development of a therapeutic medicine.

Meanwhile, Matrin-3 is a molecule which attracts attention, by recent consecutive reports of the important findings.

Matrin-3 is a 125-kDa intranuclear protein (Non Patent Literature 1, Non Patent Literature 2). Further, this molecule is known to have the function such as chromatin organisation, DNA replication, and RNA processing (Non Patent Literature 3). Matrin-3 is a molecule which has previously been analyzed little, in the field of Neuroscience. However, it has recently been reported that when there is mutation in a gene of Matrin-3, familial amyotrophic lateral sclerosis is developed (Non Patent Literature 4), and that the Matrin-3 network is essential for a homeodomain transcription program (Non Patent Literature 5).

CITATION LIST

Non-Patent Literature

NON-PATENT LITERATURE 1: Nakayasu H., Berezney R., Proc. Natl. Acad. Sci. U.S.A. 88, 10312-10316 (1991).
NON-PATENT LITERATURE 2: Belgrader P., Dey R., Berezney R., J. Biol. Chem. 266, 9893-9899 (1991).
NON-PATENT LITERATURE 3: Salton M. et al., PLoS One 6, e23882 (2011).
NON-PATENT LITERATURE 4: Skowronska-Krawczyk D. et al., Nature 514, 257-261 (2014).
NON-PATENT LITERATURE 5: Johnson J. O. et al., Nat. Neurosci. 17, 664-666 (2014).

SUMMARY OF THE INVENTION

The present inventor is the leading expert who developed the post-translational modification proteomics method which is also the patent technique (JP-A-2013-61253), concerning proteomics study.

The present inventor made an analysis using the above-mentioned post-translational modification proteomics method, in order to reveal the mechanism of neural differentiation in the brain. As a result, the present inventor succeeded in finding of as many as about 4000 novel control factors. It has been suggested that these novel control factors are involved in neural differentiation, in mouse fetal brain development.

The present inventor made an analysis of such novel control factors. As a result, among 4000 novel control factors, some molecules which play an interesting role as a control factor were found out.

Matrin-3 was included as one of the found out molecules. As a result of further study thereafter, the present inventor revealed that Matrin-3 takes charge of maintenance of undifferentiated property of neural stem cells.

That is, when neural stem cells maintain undifferentiated property, Matrin-3 exhibits a high expression amount. Simultaneously, phosphorylation of Matrin-3 has been enhanced. On the other hand, when neural stem cells exhibit neural differentiation, an expression amount of Matrin-3 reduced. Additionally, Matrin-3 has been dephosphorylated. In this way, Matrin-3 works so as to maintain neural stem cells. That is, Matrin-3 functioned in the direction of inhibition of neural differentiation.

Contrary to this role of Matrin-3, as one of molecules which promote neural differentiation, INI1 was found out.

That is, when neural stem cells maintain undifferentiated property, INI1 exhibits a low expression amount. Simultaneously, INI1 was in the dephosphorylated state. On the other hand, when neural stem cells exhibit neural differentiation, an expression amount of INI1 was increased. Additionally, phosphorylation of INI1 was enhanced.

As was confirmed in these Matrin-3 and INI1, in the brain, a stem cell maintenance factor which maintains undifferentiated property of stem cells, and a stem cell differentiation promoting factor which promotes differentiation (hereinafter, a stem cell maintenance factor and a stem cell differentiation promoting factor are collectively abbreviated as "stem cell control factor") exist. Further, the present inventor considered that the mechanism in which neural differentiation is controlled by adjustment of an expression amount of, as well as phosphorylation and dephosphorylation of this stem cell control factor (hereinafter, abbreviated as "stem cell controlling mechanism") may also exist in small cell lung cancer.

An object of the present invention under the background of the above-described circumstances is to reveal a role of the stem cell control factor including Matrin-3 in cancers exhibiting neural differentiation including small cell lung cancer, and develop a medicine useful for treating cancer and the like, based on the role.

Solution to the Problems

The present inventor intensively made a study, and as a result, found out that in small cell lung cancer, the stem cell control factor such as Matrin-3 and INI1 is expressed, and the same stem cell controlling mechanism as that of brain exists.

That is, the present inventor confirmed that expression of Matrin-3 is high in small cell lung cancer. Additionally, it was found out that neural differentiation of small cell lung cancer is controlled by regulation of an expression amount of, and phosphorylation and dephosphorylation of this Matrin-3. In addition, it was found out by the present inventor that also in INI1, when neural stem cells maintain undifferentiated property, INI1 exhibits a low expression amount, and is in the dephosphorylated state. Meanwhile, the present inventor found out that when neural stem cells exhibit neural differentiation, an expression amount of INI1 is increased, and phosphorylation of INI1 is enhanced.

By further study, the present inventor found out that proliferation of cancer cells is suppressed by suppressing Matrin-3 which functions as the stem cell maintenance factor, INI1 which functions as the differentiation promoting factor, and expression of these proteins.

This is not the easily conceivable discovery. That is, this is because proliferation of cancer can also be suppressed by suppressing an expression amount of any of proteins which play respective contradictory roles, of undifferentiated property maintenance and differentiation promotion.

As a result of further study, the present inventor found out that, in cancer cells, the stem cell maintenance factor and the differentiation promoting factor are highly expressed as compared with normal cells, and these maintain balance peculiar to cancer cells (hereinafter, the mechanism of retaining this balance is abbreviated as "cancer stem cell controlling mechanism"). Further, it was confirmed that proliferation of cancer cells can be suppressed by breaking down this cancer stem cell controlling mechanism. Thus, the invention was completed.

Furthermore, the present inventor confirmed that the stem cell maintenance factor is strongly expressed in undifferentiated cancer and neuroendocrine tumor with which stem cells are strongly involved, and the stem cell controlling mechanism similar to that of small cell lung cancer exists, and thereby, completed the invention.

The present invention includes the following configurations.

A first configuration of the present invention is a medicine for treating cancer, the medicine suppressing proliferation of cancer cells by breaking down a cancer stem cell controlling mechanism, in cancer exhibiting differentiation potency and cancer having undifferentiated property.

A second configuration of the present invention is the medicine for treating cancer according to the first configuration, wherein the breaking down of the cancer stem cell controlling mechanism is performed by suppressing an expression amount of a stem cell control factor or a phosphorylated stem cell control factor.

A third configuration of the present invention is the medicine for treating cancer according to the first or second configuration, wherein the breaking down of the cancer stem cell controlling mechanism is performed by inhibiting phosphorylation of the stem cell control factor.

A fourth configuration of the present invention is the medicine for treating cancer according to the first to third configurations, wherein the stem cell control factor is a stem cell control factor existing in a nucleus of cancer cells.

A fifth configuration of the present invention is the medicine for treating cancer according to the second configuration, wherein suppression of the expression amount of the stem cell control factor is performed by a medicine containing an anti-stem cell control factor antibody as an active ingredient.

A sixth configuration of the present invention is the medicine for treating cancer according to the second configuration, wherein suppression of the expression amount of the phosphorylated stem cell control factor is performed by a medicine containing an anti-phosphorylated stem cell control factor antibody as an active ingredient.

A seventh configuration of the present invention is the medicine for treating cancer according to the second configuration, wherein suppression of the expression amount of the stem cell control factor is performed by a medicine containing a siRNA to the stem cell control factor as an active ingredient.

An eighth configuration of the present invention is the medicine for treating cancer according to the seventh configuration, wherein the siRNA has a sequence described in SEQ ID Nos.: 1 to 6.

A ninth configuration of the present invention is the medicine for treating cancer according to the first to eighth configurations, wherein the stem cell control factor is selected from any of, or a plurality of Matrin-3, INI1, hnRNPK, MBD3, and SFRS3.

A tenth configuration of the present invention is the medicine for treating cancer according to the first to ninth configurations, wherein the cancer exhibiting the differentiation potency, and the cancer having undifferentiated property are neuroendocrine tumor.

An eleventh configuration of the present invention is the medicine for treating cancer according to the first to ninth configurations 1 to 9, wherein the cancer exhibiting the differentiation potency, and the cancer having undifferentiated property are selected from any of small cell lung cancer, leukemia, breast cancer, large intestine cancer, stomach cancer, rectum cancer, skin cancer, prostate cancer, ovary cancer, uterine body cancer, pancreas cancer, osteosarcoma, and neuroblastoma cancer.

A twelfth configuration of the present invention is a method for treating cancer, including suppressing proliferation of cancer cells by breaking down a cancer stem cell controlling mechanism in cancer exhibiting differentiation potency and cancer having undifferentiated property.

A thirteenth configuration of the present invention is a kit for extracorporeally diagnosing cancer, the kit predicting a therapeutic effect of a medicine for treating cancer, by investigating expression of a stem cell control factor in a cancer tissue.

A fourteenth configuration of the present invention is a method for predicting a therapeutic effect, including performing immunostaining of a stem cell control factor using a tissue section prepared from a biopsy sample containing cancer cells collected by biopsy, thereby, investigating expression of the stem cell control factor to predict a therapeutic effect of a medicine for treating cancer.

Effects of the Invention

According to the present invention, existence of the cancer stem cell controlling mechanism in cancer exhibiting the differentiation potency and undifferentiated cancer, including small cell lung cancer, was revealed. Thereby, it has become possible to provide a medicine useful for treating and diagnosing cancer and the like, based on the mechanism in which the proliferation mechanism which is constructed by the stem cell control factor in cancer is broken down.

BRIEF DESCRIPTION OF THE DRAWINGS

FIG. 21 is a view which was obtained by comparing the Matrin-3 immunostaining results of Merkel's cell cancer which is skin cancer exhibiting neural differentiation, and other skin cancers exhibiting no neural differentiation, using a human pathological tissue section.

DESCRIPTION OF THE EMBODIMENTS

Figure 1:
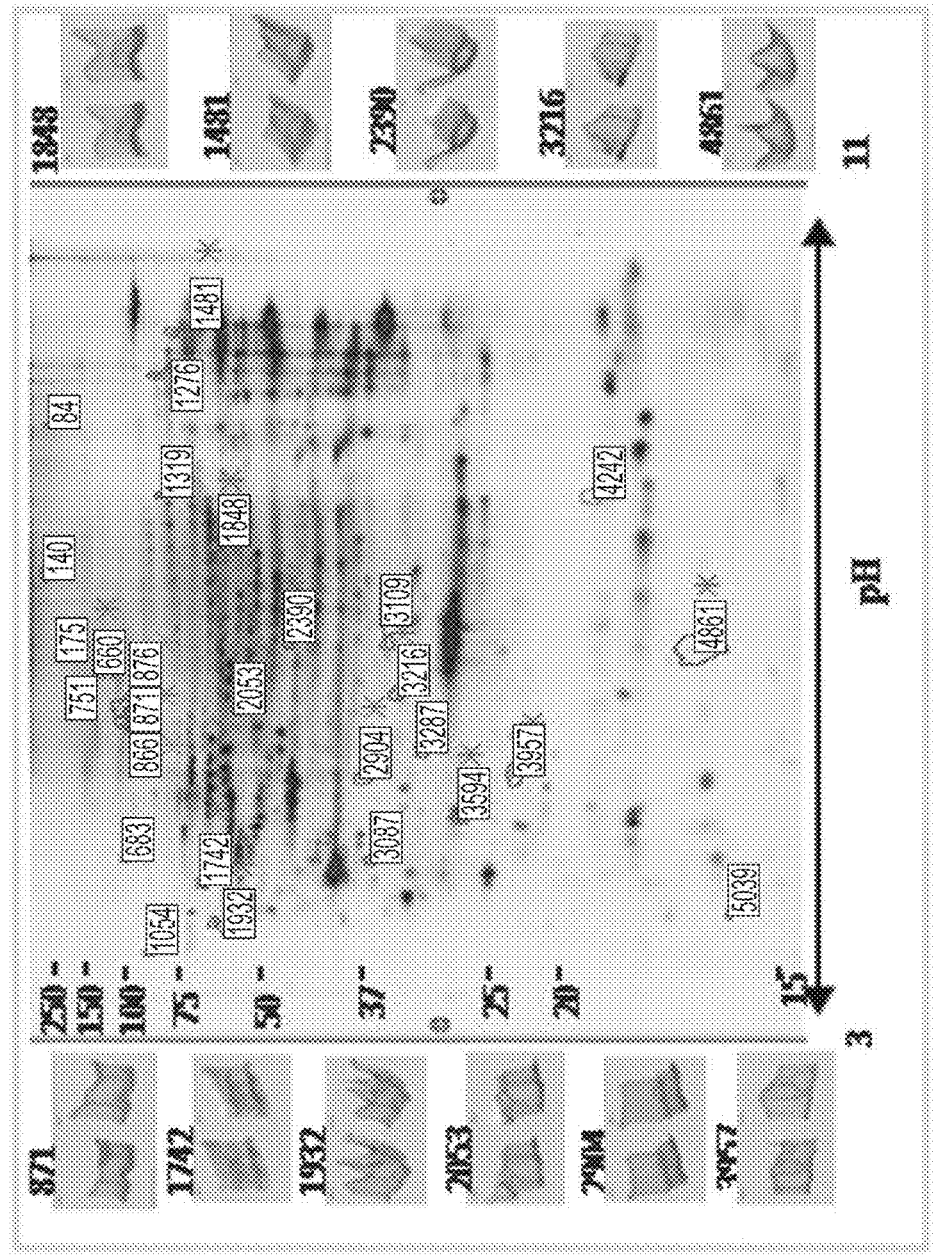
FIG. 1 is a view showing the result of two-dimensional electrophoretic analysis of nuclear proteins which were extracted from neural stem cells.

The present invention will be illustrated below.

The principle of the medicine for treating cancer and the method for treating cancer and the like of the present invention is to suppress proliferation of cancer, by breaking down the cancer stem cell controlling mechanism.

In the present invention, the cancer stem cell controlling mechanism is defined as the mechanism in which proliferativeness peculiar to cancer cells is maintained by the balance between the stem cell maintenance factor and the differentiation promoting factor, which is different from the balance of normal cells.

That is, among cancers having the cancer stem cell controlling mechanism, in cancer exhibiting the differentiation potency, the peculiar balance where expression of the stem cell maintenance factor and expression of the differentiation promoting factor are both higher as compared with normal cells is retained. Additionally, in undifferentiated cancer, the peculiar balance where expression of the stem cell maintenance factor is higher as compared with normal cells is retained. In cancer in which the cancer stem cell controlling mechanism exists, these peculiar balances of the stem cell control factor which are different from the balance of normal cells exist. In the medicine for treating cancer and the method for treating cancer of the present invention, proliferativeness of cancer is suppressed by breaking down this balance of the stem cell control factor.

In the present invention, the stem cell maintenance factor is defined as a molecule which plays a role of retaining undifferentiated property of cancer stem cells. Examples of such a stem cell maintenance factor include Matrin-3 and the like.

Additionally, in the present invention, the differentiation promoting factor is defined as a molecule which plays a role of promoting differentiation of cancer stem cells. Examples of such a differentiation promoting factor include INI1 (SWI/SNF-related matrix-associated actin-dependent regulator of chromatin subfamily B member 1), hnRNPK (Heterogeneous nuclear ribonucleoprotein K), MBD3 (Methyl-CpG-binding domain protein 3), SFRS3 (Serine/arginine-rich splicing factor 3) and the like.

Breaking down of the cancer stem cell controlling mechanism is performed by breaking down the balance of the stem cell control factor, which is retained in cancer cells.

Examples of a procedure of breaking down the balance of the stem cell control factor include the following procedures.

(1) Suppression of expression of stem cell control factor
(2) Suppression of expression of phosphorylated stem cell control factor
(3) Inhibition and suppression of phosphorylation of stem cell control factor For suppressing expression of the stem cell control factor, a variety of procedures can be adopted, as far as they can suppress expression of the stem cell control factor.

As such a suppression procedure, for example, an antibody to the stem cell control factor can be used. In this case, the procedure is not limited only to an antibody to the stem cell control factor, and a substance which is obtained by fragmenting this, or an antibody having in vivo pharmacokinetics improved by chemical modification and the like can also be used.

Additionally, as another suppression procedure, expression can be suppressed at the mRNA level using a siRNA or the like. In this case, the procedure is not limited to a siRNA itself, but a siRNA which is obtained by chemically modifying this, or a siRNA having in vivo pharmacokinetics which were improved with a liposome and the like can also be used.

One example of such a siRNA includes use of sequences disclosed in SEQ ID Nos.: 1 to 6, as an active ingredient. That is, such sequences are a siRNA to Matrin-3. These sequences act on an mRNA of Matrin-3 to suppress expression of Matrin-3 at the gene level.

In addition, in the present invention, an active ingredient is defined as a molecular form when the drug efficacy is exerted. For that reason, for example, when a siRNA or an antibody is an active ingredient, a siRNA or an antibody itself can also be used as a medicine. Additionally, an active ingredient which was drug delivery-systematized by chemical modification or a liposome and the like can also be used as a medicine.

For suppressing expression of a phosphorylated stem cell control factor, a variety of procedures can be adopted, as far as they can suppress expression of the phosphorylated stem cell control factor. Such procedures include use of an antibody to the phosphorylated stem cell control factor, and suppression of expression of a protein at the mRNA level using a siRNA and the like.

For inhibiting and suppressing phosphorylation of the stem cell control factor, a variety of procedures can be adopted, as far as they can inhibit and suppress phosphorylation of the stem cell control factor. Such procedures include a low-molecular compound which binds to a phosphorylation site to prevent phosphorylation.

It is preferable to target the stem cell control factor existing in a nucleus in cancer cells, as the stem cell control factor of the present invention. As such a stem cell control factor existing in a nucleus, a stem cell control factor having high contribution to the cancer stem cell controlling mechanism such as INI1, hnRNPK, MBD3, and SFRS3 exists. For that reason, by suppressing them and so on, proliferation of cancer can be effectively suppressed.

Cancer having the cancer stem cell controlling mechanism in the present invention is defined as cancer having a cell with the property of a stem cell, among cancer cells. Cancer exhibiting the differentiation potency or undifferentiated cancer is also included in cancer having the cancer stem cell controlling mechanism.

That is, in cancer which is a subject of the medicine for treating cancer or the method for treating cancer of the present invention, unlike normal cells, proliferativeness is maintained by the balance between the stem cell maintenance factor and the differentiation promoting factor. Cancer which is the subject can be reworded into cancer in which such a cancer cell control factor is highly expressed.

Cancer exhibiting the undifferentiated potency includes thyroid undifferentiated cancer. The malignancy is histologically and clinically high. Under the current situation, a method for treating it has not been established.

Cancer exhibiting neural differentiation includes neuroendocrine tumor, provided that neuroendocrine tumor is not limited to specific organs. That is, neuroendocrine tumor can be developed in each organ of a whole body, such as digestive tract, lung, liver, gallbladder, and pancreas.

In addition, small cell lung cancer is one of cancers represented by cancer exhibiting neural differentiation, and at the same time, exhibits undifferentiated property. That is, small cell lung cancer has both of these properties.

In this way, since cancer having the cancer stem cell controlling mechanism is highly-diversified, it is difficult to simply limit such cancer. Hence, preferably, such cancer is specified by various cancer markers, or by investigating expression of the cancer stem cell control factor.

As one example, neuroendocrine tumor expresses a neural differentiation marker or a neuroendocrine marker, such as synaptophysin, chromogranin A, and NSE (neuron specific enolase). For that reason, by investigating these markers, whether the medicine for treating cancer of the present invention can be applied or not can be confirmed.

Additionally, as another example, acute myelogenous leukemia, breast cancer, brain tumor, prostate cancer, large intestine cancer, head and neck squamous cell cancer, and pancreas cancer and the like are known as cancer having the high malignancy, which expresses a cancer stem cell marker. By investigating this cancer stem cell marker, whether the medicine for treating cancer of the present invention can be applied or not can be confirmed.

In this way, cancer which is a subject of the medicine for treating cancer or the method for treating cancer of the present invention is cancer exhibiting the differentiation potency, or undifferentiated cancer. By investigating expression of various cancer markers, or the cancer cell control factor, these cancers can be confirmed. Additionally, cancer which is a subject is not limited to cancers of specific tissues, as far as it is cancer having the cancer stem cell controlling mechanism which is manifested by various cancer markers or the cancer cell control factor. That is, any cancer among lung cancer, pancreas cancer, malignant melanoma, breast cancer, malignant lymphoma, digestive organ cancer, esophagus cancer, stomach cancer, large intestine cancer, rectum cancer, colon cancer, bile duct cancer, gallbladder cancer, liver cancer, tongue cancer, oral cavity cancer, pharynx cancer, larynx cancer, kidney cancer, ovary cancer, uterus cancer, prostate cancer, thyroid cancer, brain tumor, angioma, leukemia, neuroblastoma, retinoblastoma, myeloma, bladder tumor, sarcoma, osteosarcoma, myosarcoma, skin cancer, and Kaposi's sarcoma can be a subject of the medicine for treating cancer or the method for treating cancer of the present invention, as far as it has the cancer stem cell controlling mechanism.

A kit for extracorporeally diagnosing cancer of the present invention is characterized in that the therapeutic effect of the medicine for treating cancer is predicted by investigating expression of the stem cell control factor in a cancer tissue.

It is not necessary that expression of the stem cell control factor be particularly limited, as far as the expression can be confirmed. A variety of procedures can be adopted.

Typically, after a biopsy sample of various cancers to be evaluated is collected, a pathological section is prepared. Further, by immunostaining with an anti-stem cell control factor antibody such as an anti-Matrin-3 antibody, expression thereof can be confirmed. Alternatively, by investigating a nucleic acid such as a DNA or an mRNA, which was extracted from a pathological section or a fixed block, by rtPCR or the like, expression of the stem cell control factor can be indirectly investigated. From the result of the protein expression or nucleic acid expression, it becomes possible to predict the therapeutic effect of the medicine for treating cancer and the like of the present invention or determine the presence or absence of application. In the present invention, a kit for extracorporeal diagnosis can be constituted as such an immunostaining kit or a nucleic acid extraction kit.

Additionally, by the above-mentioned immunostaining method, the therapeutic effect of the medicine for treating cancer can be predicted. That is, a method for predicting the therapeutic effect of the present invention has the following characteristic: First, a tissue section is prepared from a biopsy sample containing cancer cells which were collected by biopsy. Further, by performing immunostaining of the stem cell control factor, expression of the stem cell control factor is investigated. In this way, the therapeutic effect of the medicine for treating cancer is predicted.

EXAMPLES

Experimental Example 1, Extraction of Differentiation Control Factor in Mouse Fetal Brain By performing analysis of nuclear proteins which are extracted from mouse fetal brain using the post-translational modification proteomics method (JP-A-2013-61253) which is the patent technique, an experiment was performed for the purpose of extracting proteins which can be involved in neural differentiation control.
<Experimental Method>
1. An experiment was performed in accordance with the method described in JP-A-2013-61253.
2. That is, a brain tissue was taken out from mouse fetal brain. Neuroepithelial cells were separated from this brain tissue, and the cells were seeded on a petri dish. Thereafter, by adding FGF2 into a medium, and culturing the cells for 5 days, neural stem cells were obtained.
3. Concerning the resulting neural stem cells, culturing was performed by separating into two conditions of the presence and absence of FGF.
4. A nuclear protein fraction was solubilized from the cultured cells using a protein extraction kit. This means that concerning this sample, separation and purification of nuclear proteins were performed by density gradient centrifugation.
5. Analysis by two-dimensional electrophoresis and image analysis of the protein extract as obtained above were performed. Thereafter, an objective protein cell spot was excised, and enzymatically treated with trypsin. Thereby, the protein was fragmented into peptides. Thereafter, identification of proteins by a mass spectrometer was performed.
<Result>
1. The result is shown in FIG. 1.
2. As a result of two-dimensional electrophoresis, 4096 proteins, expression of which varied by FGF2 stimulation, were detected.
3. Concerning a group of these proteins, identification of proteins was performed from the result of mass spectrometry. As a result of analysis, five proteins which are suggested to be strongly associated with neural differentiation were detected. These five proteins were INI1, hnRNPK, MBD3, Matrin-3, and SFRS3, respectively.

Experimental Example 2, Culturing of Neural Stem Cells in the Presence and Absence of Matrin-3-siRNA For the purpose of revealing what influence is given to differentiation of neural stem cells by Matrin-3, an experiment was performed.
<Experimental Method>
1. According to the same manner as that of Experimental Example 1, neural stem cells were obtained. In order to make it easy to observe a form of cells, upon treatment with a siRNA, a plasmid of GFP was simultaneously introduced into neural stem cells by electroporation.
2. Neural stem cells were cultured under two conditions, in the presence or absence of a siRNA of Matrin-3. A Matrin-3-siRNA purchased from Santa Cruz Biotechnology was used. Culturing was performed at the concentration adjusted at 100 pmol.
3. The catalog No. of a siRNA purchased from Santa Cruz Biotechnology is sc-62605. This has a sequence showing the effect on not only a mouse but also a human. Additionally, all of three sequences of A, B, and C have cross-reactivity with five transcript mutants of human Matrin-3 of 100%.

```
(1) sc-62605A
Sense (SEQ ID No.: 1):
GCUACCCAGUCUUUAAGUAtt

Antisense (SEQ ID No.: 2):
UACUUAAAGACUGGGUAGCtt (2) sc-62605B
Sense (SEQ ID No.: 3):
CUAGUACUUCUUCCCAUAAtt Antisense (SEQ ID No.: 4):
UUAUGGGAAGAAGUACUAGtt
```

-continued

```
(3) sc-62605C
Sense (SEQ ID No.: 5):
CCAUUUGGAGUCAUUUCAAtt

Antisense (SEQ ID No.: 6):
UUGAAAUGACUCCAAAUGGtt
```

Figure 2:
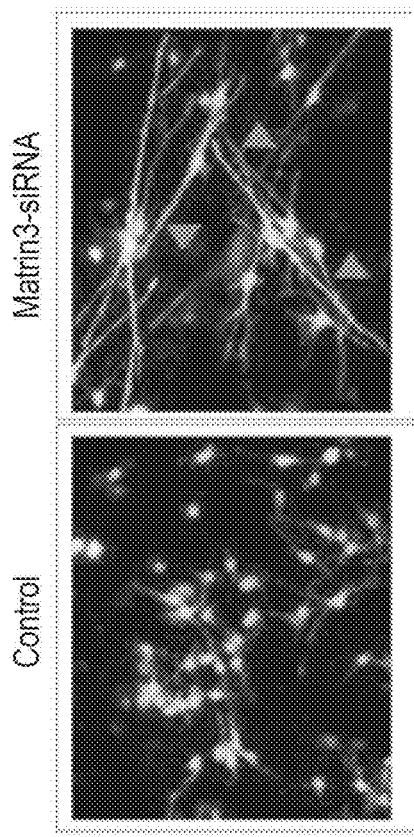
FIG. 2 is a view showing the state that neural stem cells were cultured in the presence and absence of a Matrin-3-siRNA.

4. Concerning the cultured neural stem cells, observation and photographing were performed with a fluorescent microscope.
<Result>
1. The result is shown in FIG. 2.
2. When expression of Matrin-3 is not suppressed, neutral stem cells maintained a form thereof without being differentiated. On the other hand, when a Matrin-3-siRNA exists, expression of Matrin-3 is suppressed. In this case, it was seen that neural stem cells generate neurite elongation, and differentiate into neurons, without maintaining a form thereof.
3. From these results, it was revealed that Matrin-3 is responsible for maintaining undifferentiated property in neural stem cells.

Figure 3:
FIG. 3 is a view showing the result of Matrin-3 immunostaining in a human pathological tissue.

Experimental Example 3, Immunohistological Staining of Matrin-3 Using Human Clinical Pathological Specimen For the purpose of studying to what extent Matrin-3 is expressed in small cell lung cancer exhibiting the neural differentiation potency, an experiment was performed. In the experiment, pulmonary adenocarcinoma and squamous cell lung cancer exhibiting no neural differentiation potency were compared with small cell lung cancer.
<Experimental Method>
1. According to the Kumamoto University Ethical Codes, human small cell lung cancer, human pulmonary adenocarcinoma, human squamous cell lung cancer, and a formalin-fixed block of each of them were obtained, and an experiment was performed.
2. A thin section of the block was prepared. Using an anti-Matrin-3 mouse monoclonal antibody (manufactured by LifeSpan Biosciences, Inc., No. LS-C72171) as a primary antibody, and an anti-mouse immunoglobulins-HRP antibody (manufactured by DAKO Co., Ltd.) as a secondary antibody, immunostaining was performed.
<Result>
1. The result of immunostaining is shown in FIG. 3.
2. As compared with pulmonary adenocarcinoma and squamous cell lung cancer, in small cell lung cancer, brown staining exhibiting staining of Matrin-3 strongly appeared. Thereby, it was revealed that in small cell lung cancer, expression of Matrin-3 is high, as compared with other cancers.

Experimental Example 4, Immunohistological Staining of Phosphorylated Matrin-3 Using Human Clinical Pathological Specimen For the purpose of studying to what extent phosphorylated Matrin-3 is enhanced in small cell lung cancer exhibiting the neural differentiation potency, an experiment was performed. In the experiment, pulmonary adenocarcinoma and squamous cell lung cancer which exhibit no neural differentiation potency were compared with small cell lung cancer.

Figure 4:
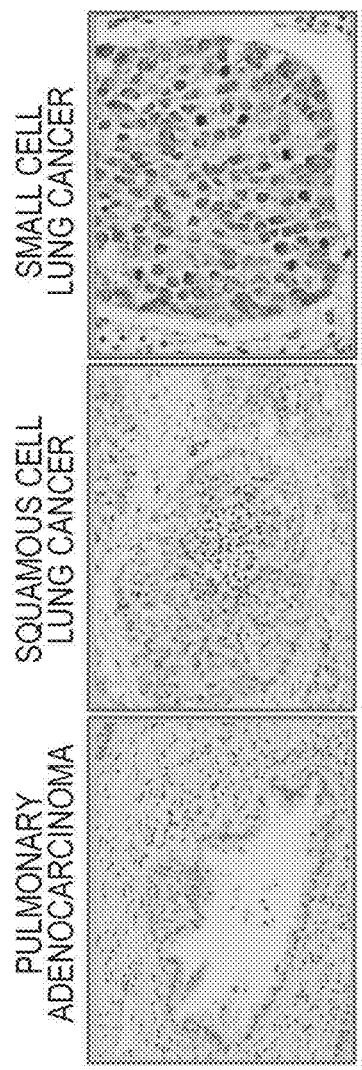
FIG. 4 is a view showing the result of phosphorylated Matrin-3 immunostaining in a human pathological tissue.

<Experimental Method>
1. An experiment was performed in accordance with Experimental Example 3.
2. As a primary antibody, an anti-phosphorylated Matrin-3 rabbit polyclonal antibody (manufactured by Bethyl Laboratories, Inc.) was used. As a secondary antibody, a polyclonal goat anti-rabbit immunoglobulins-HRP antibody (manufactured by DAKO Co., Ltd.) was used.
3. In addition, the anti-phosphorylated Matrin-3 rabbit polyclonal antibody is an antibody which specifically recognizes phosphorylation of a 208th serine residue, of a complete amino acid sequence of Matrin-3.
<Result>
1. The result of immunostaining is shown in FIG. 4.
2. As compared with pulmonary adenocarcinoma and squamous cell lung cancer, brown staining exhibiting staining of phosphorylated Matrin-3 strongly appeared, in small cell lung cancer. This revealed that phosphorylation of Matrin-3 is enhanced in small cell lung cancer, as compared with other cancers.

Experimental Example 5, Culturing of Matrin-3-shRNA-Introduced Small Cell Lung Cancer Cultured Strain For the purpose of revealing what influence is given to a suspending small cell lung cancer cultured strain (H69 cells) by Matrin-3, an experiment was performed.
<Experimental Method>
1. Concerning H69 cells, introduction of a Matrin-3-shRNA (manufactured by OnGene Technologies, Inc.) was performed, and culturing was performed.
As a comparative control, also concerning H69 cells in which a control shRNA having no siRNA to Matrin-3 had been introduced, culturing was performed under the same condition.
2. Four kinds of sequences of a shRNA of Matrin-3 are shown below.

```
(1) Matrin-3-shRNA1
                                    (SEQ ID No.: 7)
TGAGTTCTTCATTGAATCAACAAGGAGCT (2) Matrin-3-shRNA2
                                    (SEQ ID No.: 8)
TATCCAGAGGACAAGATTACTCCTGAGAA (3) Matrin-3-shRNA3
                                    (SEQ ID No.: 9)
GATTTGCCAGTTCATTCTAATAAGGAGTG (4) Matrin-3-shRNA4
                                   (SEQ ID No.: 10)
AAGTATGCCAGCATCTCTTGGAAGGATGA
```

Figure 5:
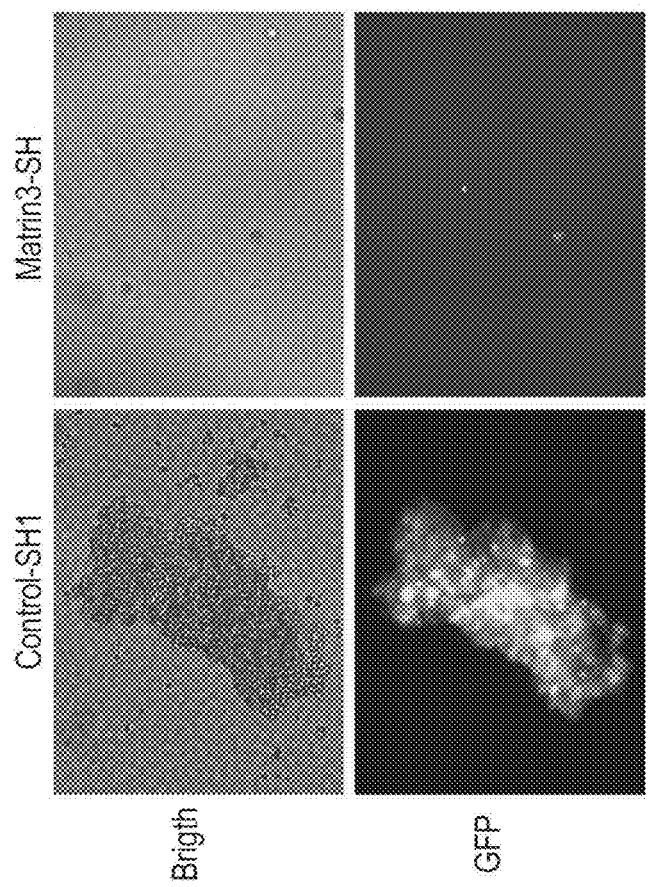
FIG. 5 is a view showing the state of a small cell lung cancer cultured strain with a Matrin-3-shRNA introduced therein.
Figure 6:
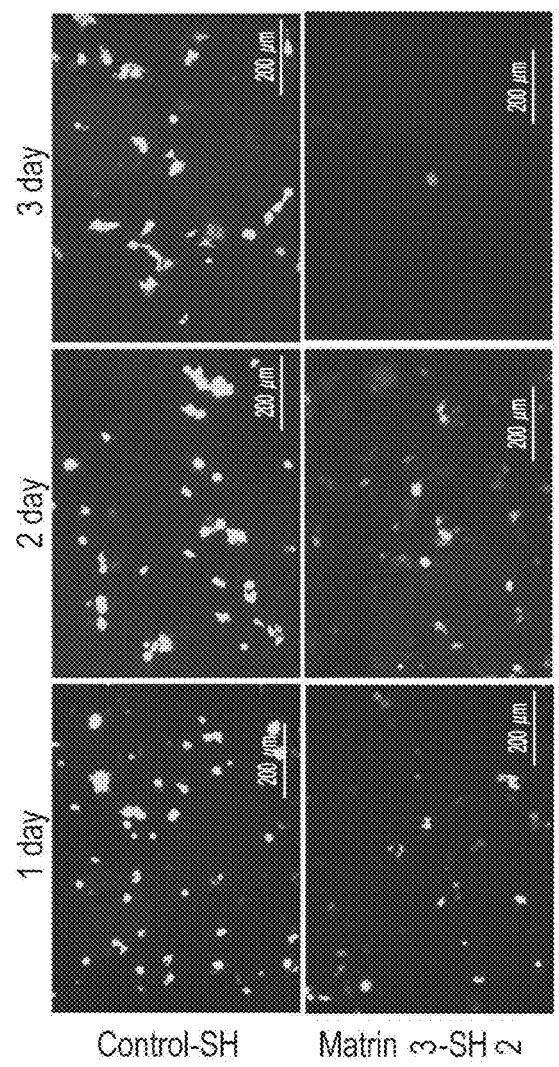
FIG. 6 is a view showing the state of a small cell lung cancer cultured strain having anti-cancer agent resistance, with a Matrin-3-shRNA introduced therein.

3. Concerning each of the cultured cells, observation and photographing were performed with a microscope.
<Experimental Result>
1. The result is shown in FIG. 5. In the figure, an upper part shows the result of observation with a light microscope, and in the figure, a lower part shows the result of observation with a fluorescent microscope.
2. In H69 cells in which a Matrin-3-shRNA had been introduced, the proliferating ability of the cells was reduced, as compared with a control. Additionally, concerning these cells, it was seen that a small amount of the cells establish a stable strain.

3. These results revealed that in H69 cells, proliferation of the cells is suppressed by suppressing expression of Matrin-3.

Experimental Example 6, Culturing of Matrin-3-shRNA-Introduced Anti-Cancer Agent Resistant Cancer Cell Strain For the purpose of revealing what influence is given to a small cell lung cancer cultured strain (H69AR cells) having resistance to doxorubicin which is an anti-cancer agent, by Matrin-3, an experiment was performed.
<Experimental Method>
1. A Matrin-3-shRNA (manufactured by OnGene Technologies, Inc.) was introduced into H69AR cells. Thereafter, the H69AR cells were cultured. As a comparative control, H69AR cells in which a control shRNA having no siRNA to Matrin-3 had been introduced were cultured under the same condition.
2. Each of the culture cells was observed and photographed with a fluorescent microscope.
<Experimental Result>
1. The result is shown in FIG. 5.
2. There was no change in the cell number of H69AR cells in which a Matrin-3-shRNA had not been introduced. Additionally, a form thereof was also maintained. On the other hand, H69AR cells in which a Matrin-3-shRNA had been introduced rapidly decreased, and almost all of them died 3 days after culturing.
3. These results revealed that H69AR cells die by suppressing expression of Matrin-3.

Experimental Example 7, Study in Small Cell Lung Cancer-Transplanted Mouse

Figure 7:
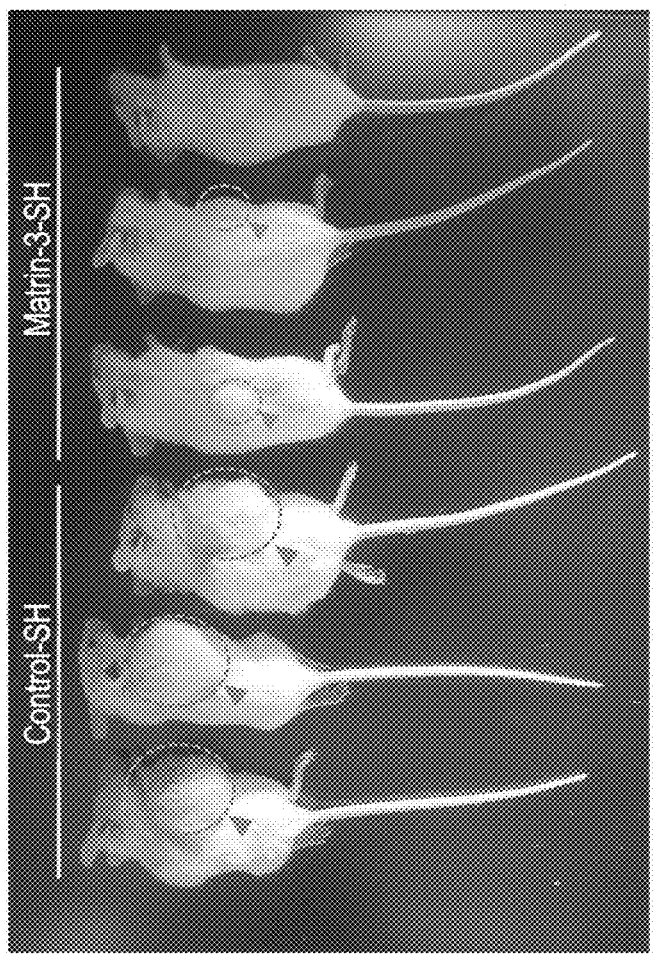
FIG. 7 is a view showing the state of a mouse subcutaneously transplanted with a Matrin-3-deficient small cell lung cancer cultured strain.
Figure 8:
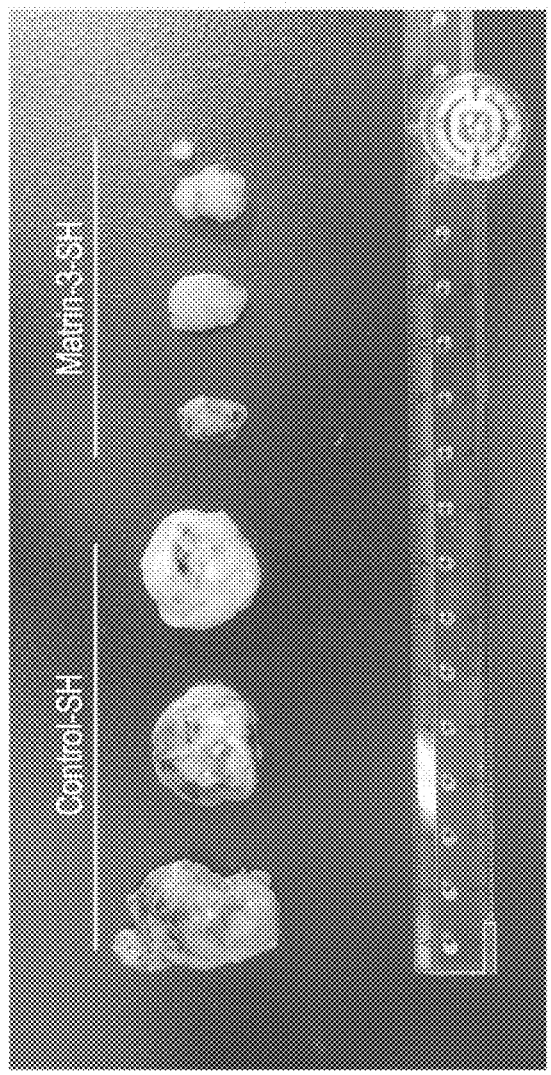
FIG. 8 is a view showing the state of tumor which was isolated from a mouse subcutaneously transplanted with a Matrin-3-deficient small cell lung cancer cultured strain.
Figure 9:
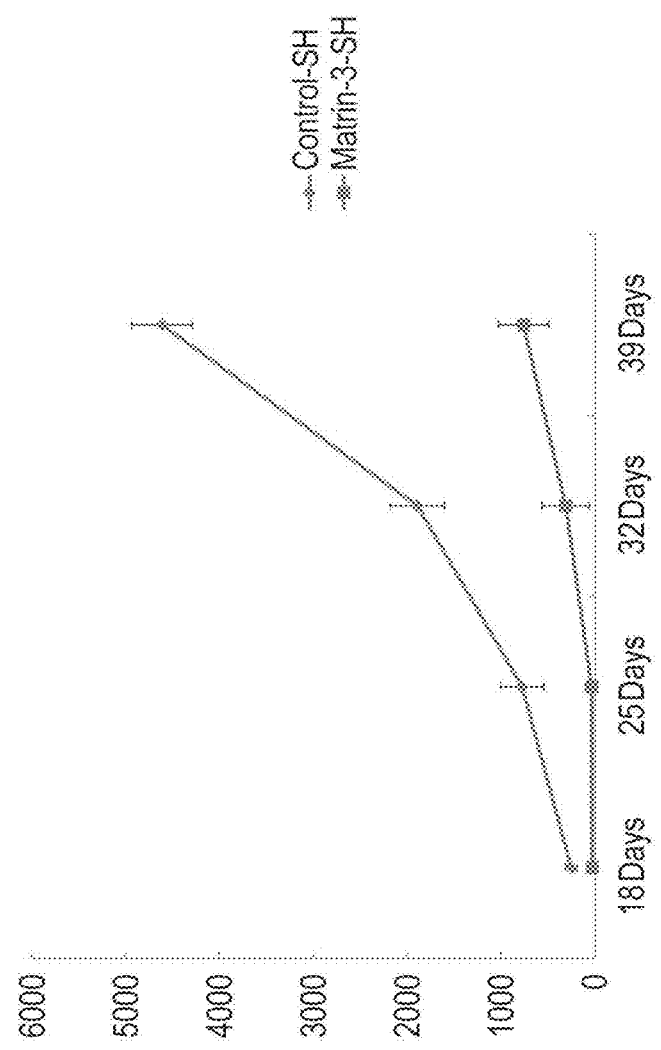
FIG. 9 is a view showing change with time in the size of tumor which was isolated from a mouse subcutaneously transplanted with a Matrin-3-deficient small cell lung cancer cultured strain.

The Matrin-3-deficient small cell lung cancer cultured strain obtained in Experimental Example 5 was subcutaneously translated into highly immunodeficient mice. For the purpose of observing these mice with time, thereby, investigating the state of proliferation thereof and the tumor forming ability thereof, an experiment was performed.
<Experimental Method>
1. The Matrin-3-deficient small cell lung cancer cultured strain obtained in Experimental Example 5 was subcutaneously transplanted into highly immunodeficient mice. The cells were subcutaneously transplanted at $2\times10^6$ per one Rag2-/-/Jak3-/-mouse which is a highly immunodeficient mouse. As a comparative control, the control cultured strain used in Experimental Example 5 was subcutaneously transplanted.
2. After subcutaneous transplantation, tumor was taken out, the state of appearance thereof was confirmed, and at the same time, the tumor size was measured.
1. FIG. 7 is a view showing the state of a mouse 39 days after subcutaneous transplantation. As seen from the figure, in a mouse in which a Matrin-3-deficient small cell lung cancer cultured strain was used, it was seen that the size of tumor is smaller, as compared with the control.
2. FIG. 8 is a view showing appearance of tumor which was isolated from a mouse 39 days after subcutaneous transplantation. In this way, in a mouse in which a Matrin-3-deficient small cell lung cancer cultured strain was used, it was seen that proliferation of tumor was suppressed, as compared with the control.
3. FIG. 9 is a view showing change with time in the size of tumor which was isolated from a mouse. In this way, also in a mouse in which a Matrin-3-deficient small cell lung cancer cultured strain was used, increase in the tumor size occurs. However, it was seen that the increase is about ⅕ as compared with the control, 39 days after subcutaneous transplantation.

Figure 10:
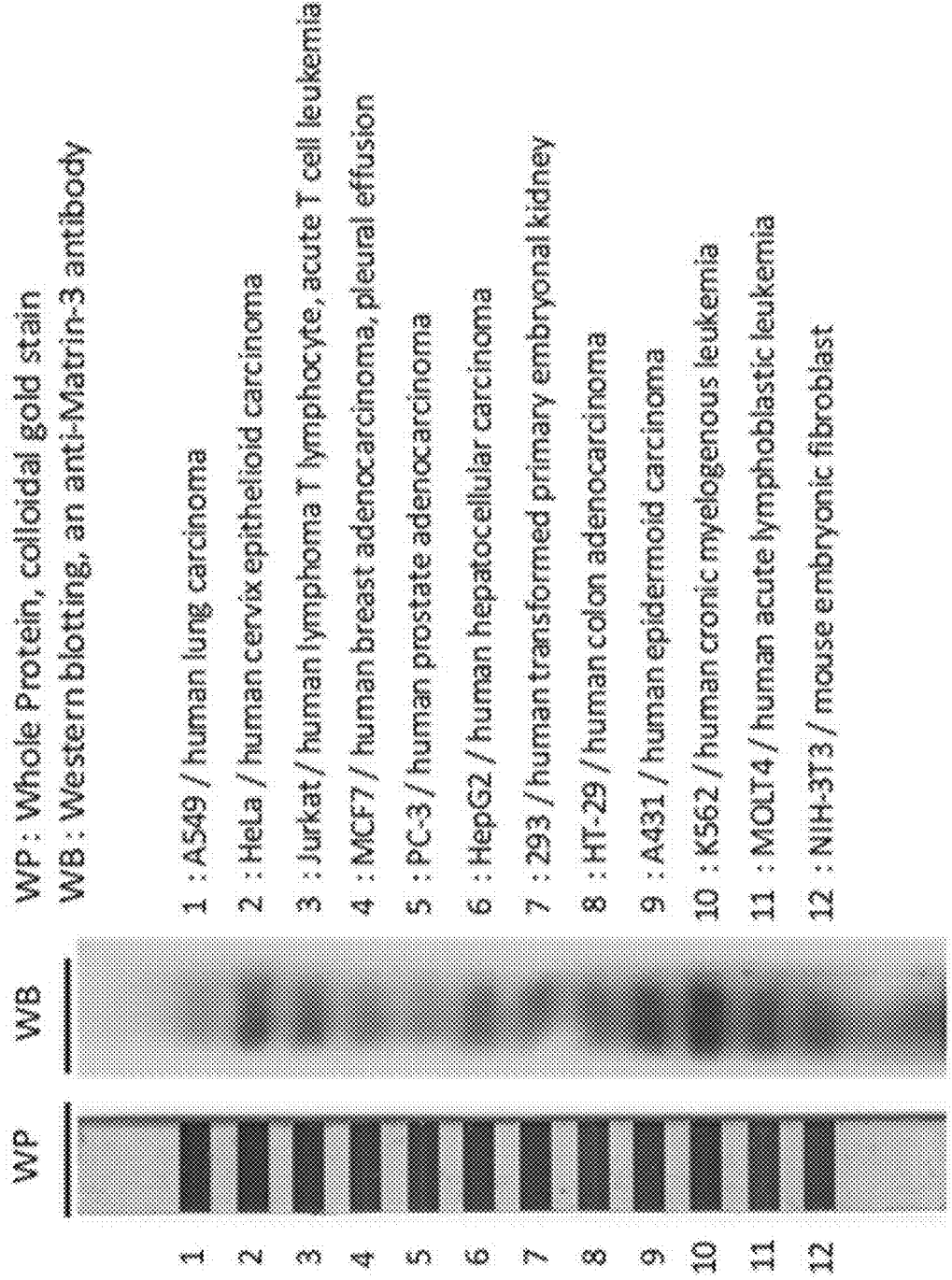
FIG. 10 is a view showing the result of Western blotting using an anti-Matrin-3 antibody, in a dipstick array in which protein extracts of a plurality of cancer cell cultured strains were blotted on a membrane.
Figure 11:
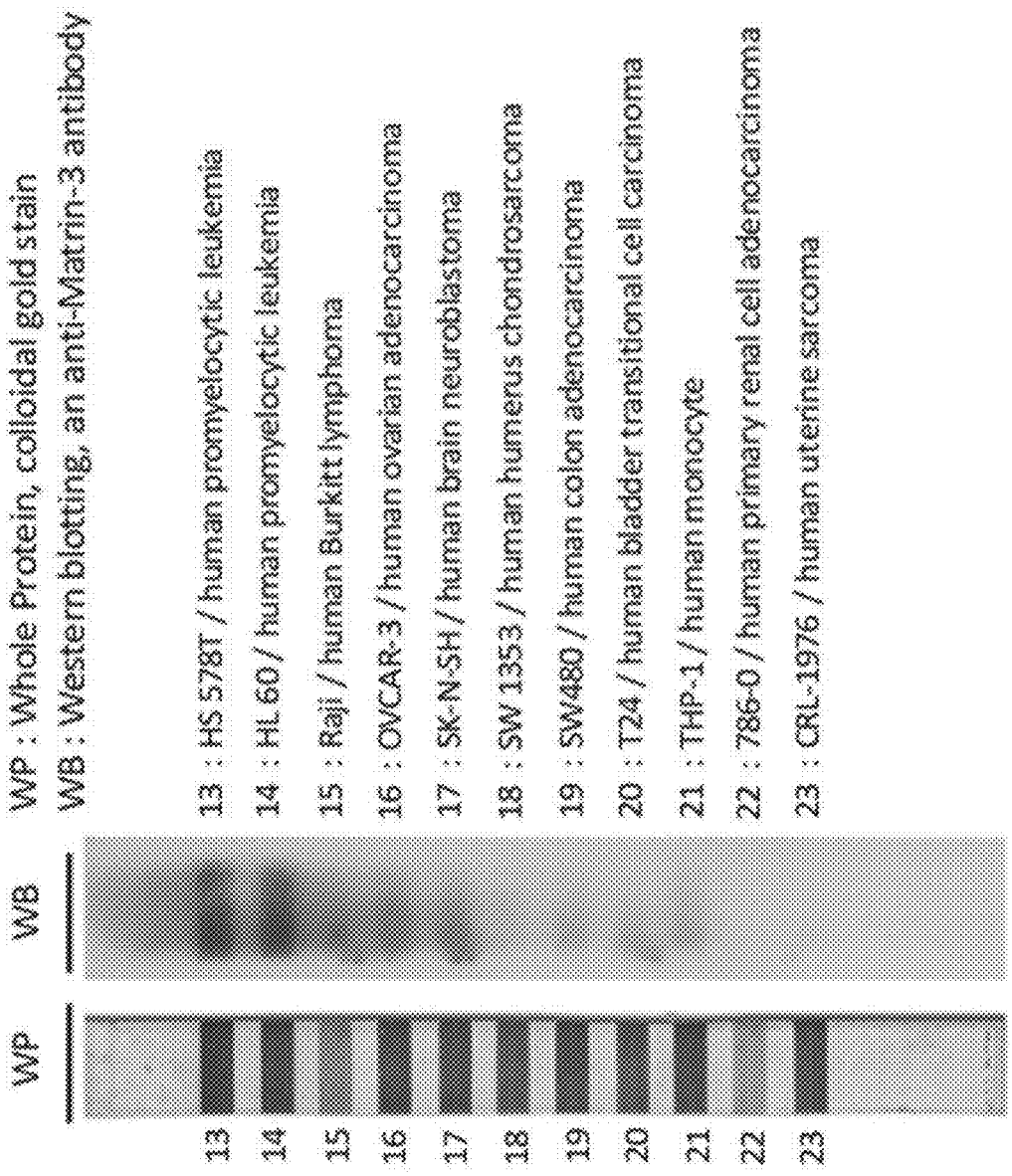
FIG. 11 is a view showing the result of Western blotting using an anti-Matrin-3 antibody, in a dipstick array in which protein extracts of a plurality of cancer cell cultured strains were blotted on a membrane.
Figure 12:
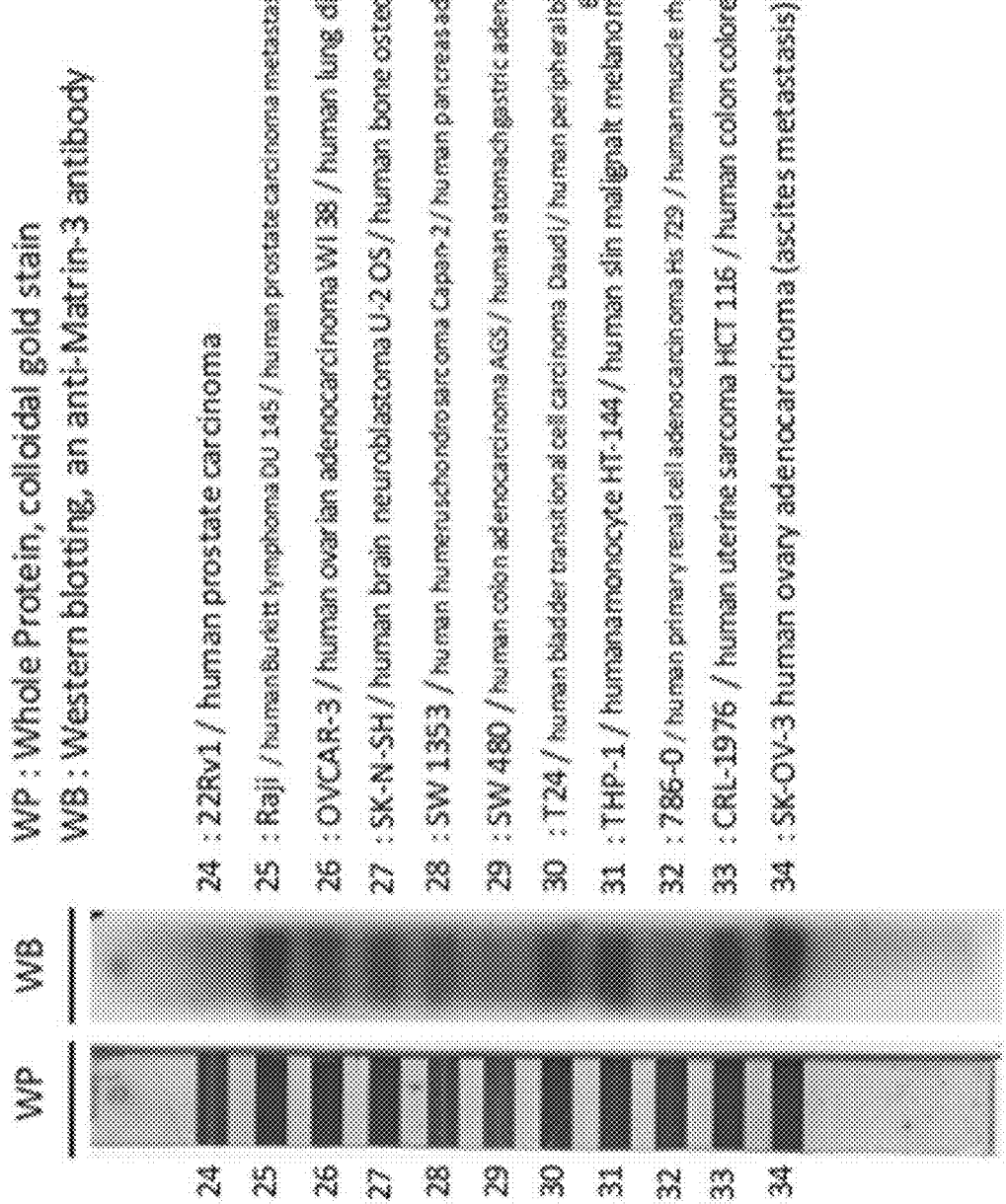
FIG. 12 is a view showing the result of Western blotting using an anti-Matrin-3 antibody, in a dipstick array in which protein extracts of a plurality of cancer cell cultured strains were blotted on a membrane.

Experimental Example 8, Analysis of Expression Profile of Matrin-3 in Various Cancers For the purpose of investigating in what cancer Matrin-3 is expressed, an experiment was performed.
<Experimental Method>
1. Using a dipstick array (manufactured by Protein Biotechnologies Inc., catalog No. SLC-1, SLC-2, SLC-3) in which protein extracts of a plurality of cell cultured strains of cancers such as leukemia, breast cancer, large intestine cancer, and prostate cancer were blotted on a membrane, Western blotting was performed.
2. As a primary antibody for specifically detecting Matrin-3, an anti-Matrin-3 mouse monoclonal antibody (manufactured by LifeSpan Biosciences, Inc., No. LS-C72171) was used. Additionally, as a secondary antibody, an anti-mouse antibody labelled with HRP (manufactured by GE Healthcare) was used.
3. For blocking, 5% skim milk was used. Additionally, detection was performed at the dilution ratio of the primary antibody of 500.
4. For detecting a signal of Matrin-3, catalog No. RPN2209ECL, Western Blotting Detection Reagents of GE Healthcare were used.
5. In addition, the dipstick array after Western blotting was stained with a gold colloid, and the detection intensity of the total amount of proteins of various cancer cell cultured strains was used as a subject to be compared.
<Result>
1. The result is shown in FIG. 10 to FIG. 12. In each figure, WB on a right side shows the result of detection with an anti-Matrin-3 antibody. Additionally, WP on a left side shows the result of detection with a gold colloid.
2. The result of FIG. 10 revealed that Matrin-3 is also expressed in cancer such as leukemia, breast cancer, large intestine cancer, and prostate cancer.
3. The result of FIG. 11 revealed that Matrin-3 is also expressed in cancer such as ovary cancer, and uterine body cancer.
4. The result of FIG. 12 revealed that Matrin-3 is also expressed in cancer such as pancreas cancer, osteosarcoma, and neuroblastoma.

Experimental Example 9, Analysis of Expression Profile of Matrin-3, INI1, MBD3, SFRS3, and hnRNPK in Lung Cancer Cultured Strain Using Western Blotting Method As a result of Experimental Example 1, 4096 proteins were detected (FIG. 1). Among them, five proteins which are suggested to be strongly associated with neural differentiation control were extracted. For the purpose of investigating what expression style is taken by INI1, hnRNPK, MBD3, Matrin-3, and SFRS3 which are these extracted five proteins in a lung cancer cultured strain, an experiment was performed.
<Experimental Method>
1. Using a Western blotting method, analysis of an expression profile of INI1, hnRNPK, MBD3, Matrin-3, and SFRS3 in small cell lung cancer cultured strains (H69, H889, and H69AR), and non-small cell cancer cultured strains (A549, H358, CALU6, H226, and H2170) was performed. Non-small cell cancer cultured strains (A549, H358, CALU6, H226, and H2170) include cultured strains of pulmonary adenocarcinoma, and squamous cell lung cancer.

2. Small cell lung cancer cultured strains (H69, H889, and H69AR), and non-small cell cancer cultured strains (A549, H358, CALU6, H226, and H2170) were cultured, and proteins were extracted. Thereafter, proteins were separated on gel by SDS-PAGE. Thereafter, proteins were transferred to a membrane for Western blotting (nitrocellulose membrane).

3. As a primary antibody for specifically detecting INI1, hnRNPK, MBD3, Matrin-3, and SFRS3, an anti-INI1 rabbit polyclonal antibody (manufactured by Santa Cruz Biotechnology, No. sc-13055), an anti-hnRNPK mouse monoclonal antibody (manufactured by Santa Cruz Biotechnology, No. sc-53620), an anti-MBD3 mouse monoclonal antibody (manufactured by Santa Cruz Biotechnology, No. sc-166319), an anti-Matrin-3 mouse monoclonal antibody (manufactured by LifeSpan Biosciences, Inc., No. LS-C72171), and an anti-SFRS3 rabbit polyclonal antibody (manufactured by Abcam plc, No. ab73891) were used, respectively. Additionally, as a secondary antibody, an anti-mouse antibody (manufactured by GE Healthcare) and an anti-rabbit antibody (manufactured by GE Healthcare) which were labelled with HRP depending on an animal species of respective primary antibodies were used. For blocking, 0.5% to 5% skim milk was used depending on each primary antibody. Additionally, the dilution ratio of the primary antibody at detection was 500 in an anti-Matrin-3 antibody and an anti-INI1 antibody, 200 in an anti-MBD3 antibody and an anti-hnRNPK antibody, and 2000 in an anti-SFRS3 antibody.

Figure 13:
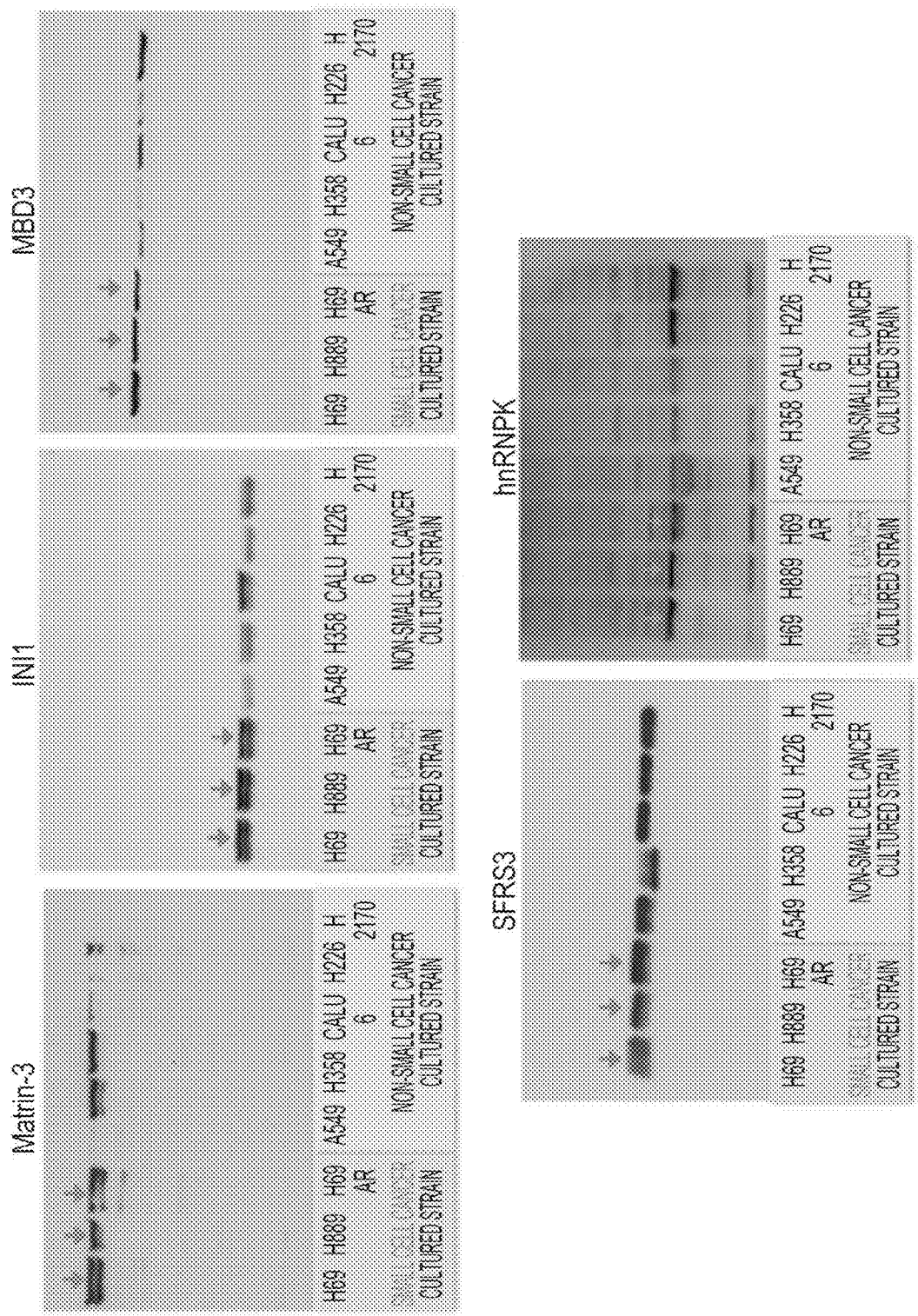
FIG. 13 is a view showing the result of analysis of an expression profile of the cancer stem cell control factor in a lung cancer cultured strain using a Western blotting method.

4. For detecting a signal of INI1, hnRNPK, MBD3, Matrin-3, and SFRS3, catalog No. RPN2209 ECL, Western Blotting Detection Reagents of GE Healthcare were used.
<Result>
1. The result is shown in FIG. 13. The result of detection with an anti-Matrin-3 antibody is shown. As a result, it was revealed that Matrin-3 exhibits particularly strong expression in a small cell lung cancer cultured strain.

2. Among the results of FIG. 13, the result of detection with an anti-INI1 antibody is shown. Additionally, FIG. 14 is an enlarged view of the result of INI1.

(1) FIG. 13 revealed that INI1 exhibits particularly strong expression in a small cell lung cancer cultured strain.

Figure 14:
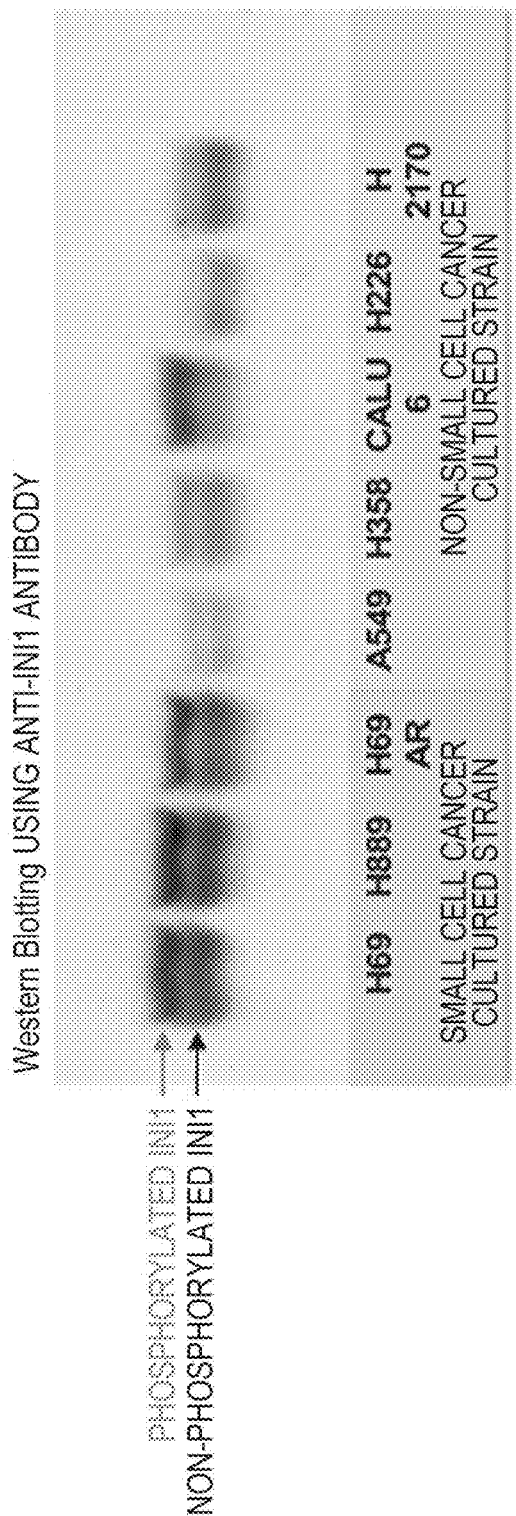
FIG. 14 is an enlarged view showing the result of analysis of an expression profile of INI1 in a lung cancer cultured strain using a Western blotting method.

(2) From FIG. 14, concerning INI1, two bands exhibiting an INI1-positive reaction were recognized. This strongly suggested a possibility that a part of INI1 is phosphorylated, and INI1 itself and phosphorylated INI1 are detected. That is, when INI1 is phosphorylated, a molecular weight is increased by about 79 Da, by modification of a phosphate group with a protein. For that reason, by a slowed electrophoretic speed, two bands are observed on SDS-PAGE. Hence, it was strongly suggested that out of the two bands, an upper band is phosphorylated INI1 and a lower band is non-phosphorylated INI1.

3. Among the results of FIG. 13, the result of detection with an anti-MBD3 antibody is shown. As a result, it was revealed that MBD3 exhibits particularly strong expression in a small cell lung cancer cultured strain.

4. Among the results of FIG. 13, the result of detection with an anti-SFRS3 antibody is shown. As a result, it was revealed that SFRS3 exhibits particularly strong expression in a small cell lung cancer cultured strain. In addition, expression was also recognized in a non-small cell lung cancer.

5. Among the results of FIG. 13, the result of detection with an anti-hnPNPK antibody is shown. As a result, it was revealed that hnRNPK exhibits particularly strong expression in a small cell lung cancer cultured strain.

Figure 15:
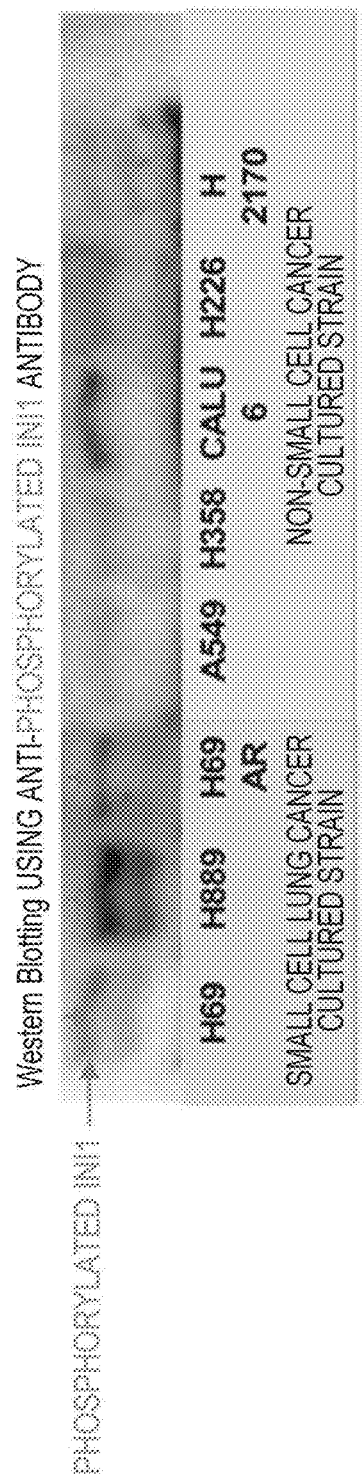
FIG. 15 is a view showing the result of analysis of an expression profile of phosphorylated INI1 in a lung cancer cultured strain using a Western blotting method.

Experimental Example 10, Analysis of Phosphorylated INI1 in Small Cell Lung Cancer Cultured Strain The result of Experimental Example 9 suggested a possibility that INI1 is phosphorylated. Additionally, in the previous report, it has been reported that serine 129 of INI1 is phosphorylated (Matsuoka S., et al., Science 316: 1160-1166 (2007)). Then, a rabbit polyclonal antibody specifically recognizing phosphorylation of serine 129 of INI1 was prepared, and this antibody was used to study enhancement of phosphorylation of INI1 in a lung cancer cultured strain.
<Experimental Method>
According to the same manner as that of Experimental Example 9, an experiment was performed. Using only an anti-phosphorylated (serine 129) INI1 antibody as a primary antibody, an experiment was performed.
<Result>
1. The result is shown in FIG. 15.

2. A band of phosphorylated INI1 is strongly detected. It was revealed that phosphorylation of INI1 is enhanced in a small cell lung cancer cultured strain.

3. Additionally, in FIG. 15, a strong positive reaction is shown with an anti-phosphorylated antibody, on a band of phosphorylated INI1 corresponding to an upper band. This confirmed that an upper band which was detected in FIG. 14 is phosphorylated INI1.

4. Furthermore, enhancement of phosphorylation of INI1 showed a strong positive reaction, particularly, in a small cell lung cancer exhibiting neural differentiation.

Experimental Example 11, Evaluation of Proliferating Ability of Small Cell Lung Cancer Cultured Strain in Presence or Absence of INI1-siRNA For the purpose of revealing what influence is given by INI1 to proliferation of a small cell lung cancer cultured strain, an experiment was performed. In the present experiment, an experiment was performed using, as an index, Ki67 as a cell proliferation marker.
<Experimental Method>
1. For an experiment, a suspending small cell lung cancer cultured strain (H69) was used. In order to make it easy to observe a form of cells, upon treatment with a siRNA, a plasmid of GFP was simultaneously introduced into H69 cells as a small cell lung cancer cultured strain by electroporation.

2. H69 cells as a small cell lung cancer cultured strain were cultured under two conditions, in the presence or absence of a siRNA of INI1. An INI1-siRNA purchased from Santa Cruz Biotechnology was used. Culturing was performed at the concentration adjusted at 100 pmol. No-treat is cells in which neither a control-siRNA nor an INI1-siRNA is introduced, that is, only GFP is introduced.

Catalog No. of a siRNA purchased from Santa Cruz Biotechnology is sc-35670. This has a sequence exhibiting the effect on not only a mouse but also a human.

(1) sc-35670A
Sense (SEQ ID No.: 11):
GCAAUGACGAGAAGUACAAtt

Antisense (SEQ ID No.: 12):
UUGUACUUCUCGUCAUUGCtt (2) sc-35670B
Sense (SEQ ID No.: 13):
GGAACAUGAAUGAGAAGCUtt Antisense (SEQ ID No.: 14):
AGCUUCUCAUUCAUGUUCCtt (3) sc-35670C
Sense (SEQ ID No.: 15):
CCACAGACAGCAUCCUAGAtt Antisense (SEQ ID No.: 16):
UCUAGGAUGCUGUCUGUGGtt 3. Cells which had been recovered 72 hours after treatment with a siRNA were fixed.

4. In order to evaluate the proliferating ability of the cells, the cells were stained using a Ki67 mouse monoclonal antibody (BD Pharmingen, Inc.) which is a cell proliferation marker. For staining a nucleus, DAPI (Sigma-Aldrich) was used. Concerning cells in which a siRNA was introduced, the cells were stained using an anti-GFP rabbit polyclonal antibody (Sigma-Aldrich). Using an anti-rabbit Alexa 488 antibody, and an anti-mouse Alexa 568 antibody as a secondary antibody, fluorescent staining was performed.

5. A fluorescent signal was observed using a fluorescent microscope of Olympus Corporation.

<Result>

Figure 16:
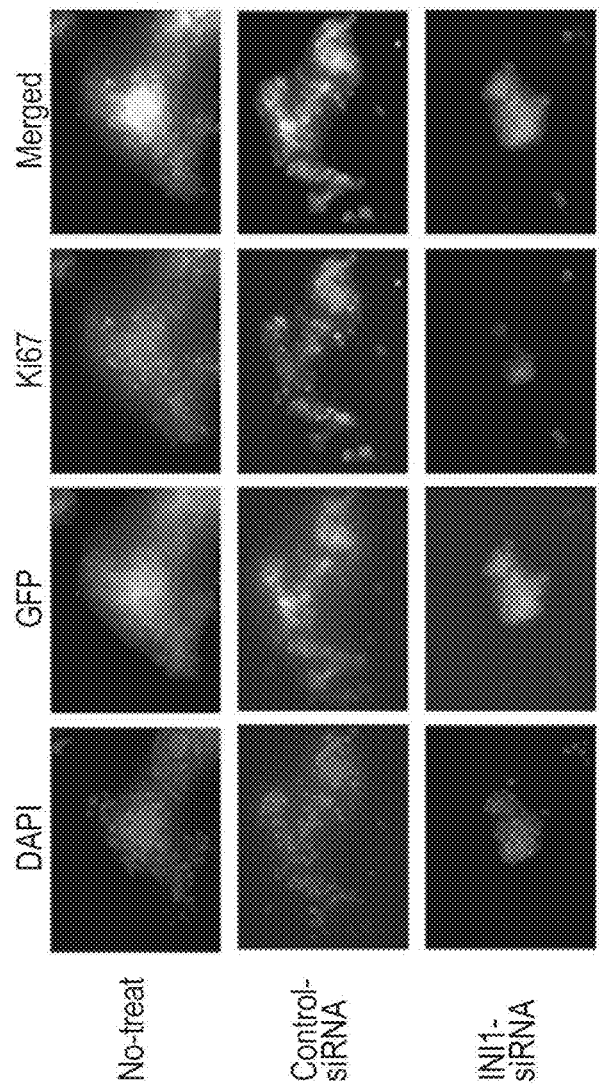
FIG. 16 is a view which was obtained by investigating what influences is given by INI1 to proliferation of a small cell lung cancer cultured strain by image analysis, using an INI1-siRNA employing a cell proliferation marker, Ki67, as an index.

1. The result is shown in FIG. 16. In addition, an image which is described as Merged is an image which was obtained by pseudo-coloring images photographed with respective fluorescent signals, and fusing the pseudo-colored images on a computer.

2. In H69 cells in which an INI1-siRNA was introduced, the number of Ki67-positive cells was reduced, as compared with a control group. This suggests that the proliferating ability of H69 cells was reduced. These results revealed that proliferation of H69 cells is suppressed by suppressing expression of INI1.

Figure 17:
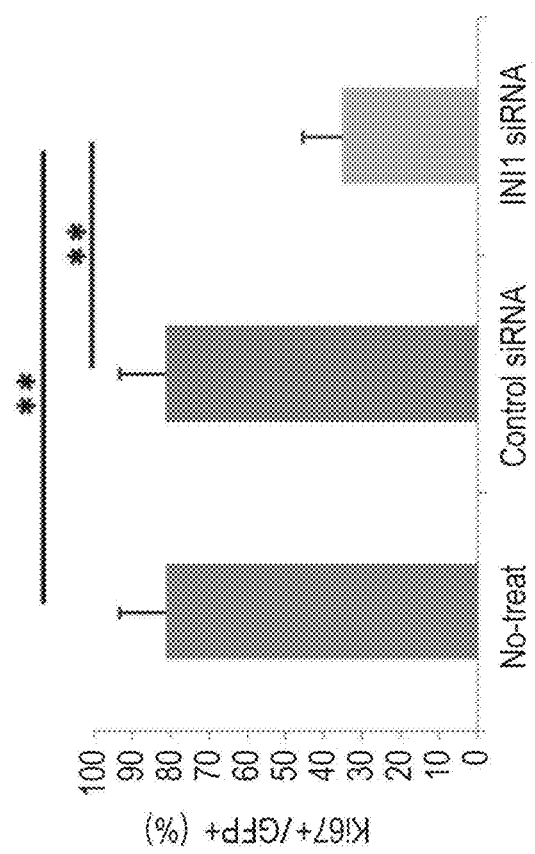
FIG. 17 is a view which was obtained by investigating what influence is given by INI1 to proliferation of a small cell lung cancer cultured strain by image analysis, using an INI1-siRNA employing a cell proliferation marker, Ki67, as an index, and quantifying this with the fluorescent intensity, followed by comparison.

3. FIG. 17 shows the result which is obtained by counting Ki67-positive cells in GFP-positive cells after cell staining, and statistically processing the count by a Student t-test. * shows that there was a statistically significant difference between groups at P<0.01. It was revealed that in small cell lung cancer cultured strain H69 cells with an INI1-siRNA introduced therein, Ki67-positive cells are decreased, as compared with a group of No-treat, Control-siRNA.

Experimental Example 12, Evaluation of Neural Differentiation of Small Cell Lung Cancer Cultured Strain in the Presence or Absence of INI1-siRNA For the purpose of revealing what influence is given by INI1 to neural differentiation control of a small cell lung cancer cultured strain, an experiment was performed. In the present experiment, an experiment was performed using, as an index, CGA (Chromogranin A) which is a neural differentiation marker.

<Experimental Method>

1. For an experiment, a suspending small cell lung cancer cultured strain (H69) was used. In order to make it easy to observe a form of cells, upon treatment with a siRNA, a plasmid of GFP was simultaneously introduced into H69 cells as a small cell lung cancer cultured strain by electroporation.

2. H69 cells as a small cell lung cancer cultured strain were cultured under two conditions, in the presence or absence of a siRNA of INI1. An INI1-siRNA purchased from Santa Cruz Biotechnology was used. Culturing was performed at the concentration adjusted at 100 pmol. No-treat is cells in which neither a Control-siRNA nor an INI1-siRNA is introduced, that is, only GFP is introduced.

3. Catalog No. of a siRNA purchased from Santa Cruz Biotechnology is sc-35670. This has a sequence exhibiting the effect on not only a mouse but also a human.

4. Cells which had been recovered 72 hours after treatment with a siRNA were fixed.

5. In order to evaluate the neural differentiation potency of H69 cells, the cells were stained using a CGA (Chromogranin A) rabbit polyclonal antibody (Santa Cruz Biotechnology) which is a neural differentiation marker of a small cell lung cancer. For staining a nucleus, DAPI (Sigma-Aldrich) was used. Concerning cells with a siRNA introduced therein, the cells were stained using an anti-GFP mouse monoclonal antibody (Sigma-Aldrich). Using an anti-mouse Alexa 488 antibody, and an anti-rabbit Alexa 568 antibody as a secondary antibody, immunostaining was performed.

6. A fluorescent signal was observed using a fluorescent microscope of Olympus Corporation.

<Result>

Figure 18:
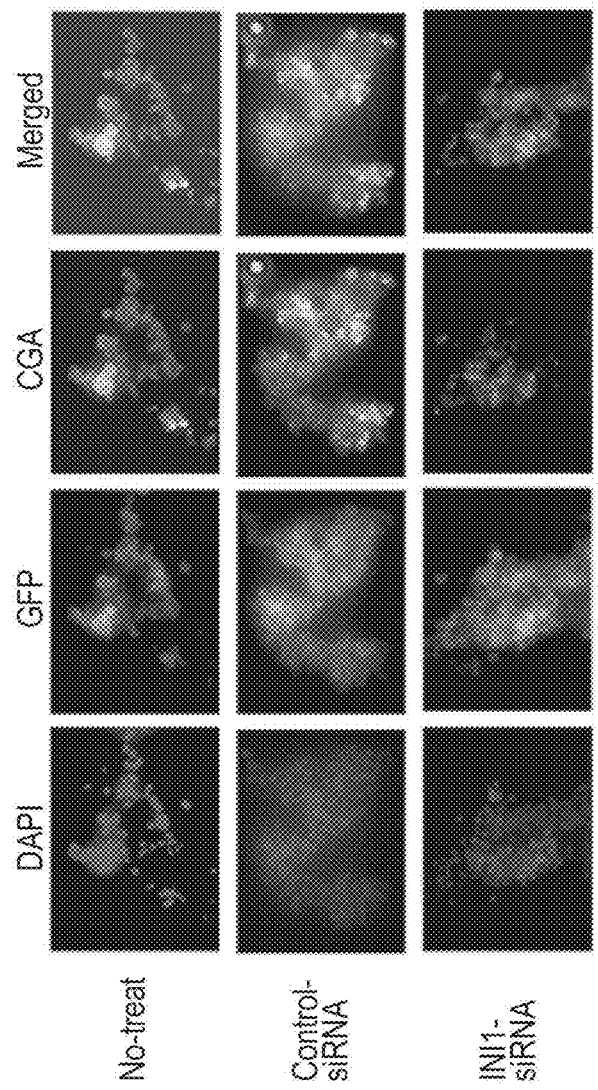
FIG. 18 is a view which was obtained by investigating what influences is given by INI1 to neural differentiation of a small cell lung cancer cultured strain by image analysis, using an INI1-siRNA employing a neural differentiation marker, CGA, as an index.

1. The result is shown in FIG. 18. An image which is described as Merged is an image obtained by pseudo-coloring images photographed with respective fluorescent signals, and fusing the pseudo-colored images on a computer.

2. In H69 cells with an INI1-siRNA introduced therein, the number of CGA-positive cells was reduced, as compared with a control group. This suggests that the neural differentiation potency of H69 cells was reduced. These results revealed that neural differentiation of H69 cells is suppressed by suppressing expression of INI1.

Figure 19:
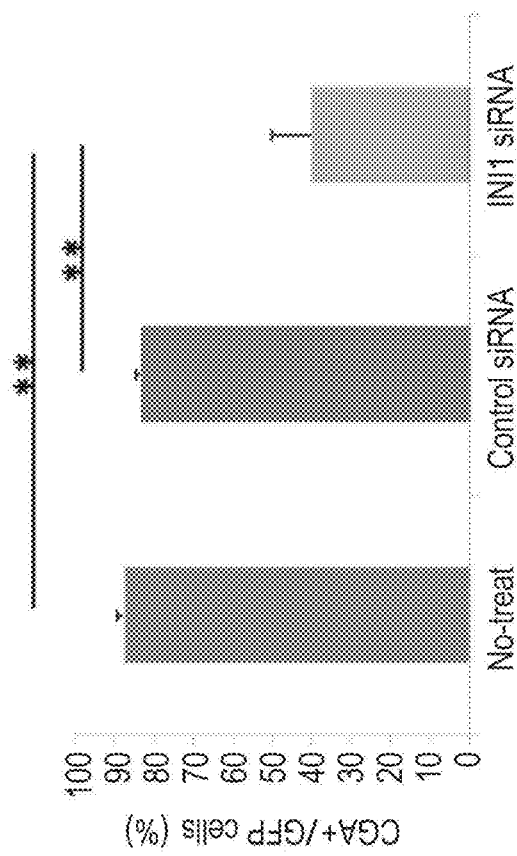
FIG. 19 is a view which was obtained by investigating what influence is given by INI1 to neural differentiation of a small cell lung cancer cultured strain by image analysis, using an INI1-siRNA employing a neural differentiation marker, CGA, as an index, and quantifying this with the fluorescent intensity, followed by comparison.

3. FIG. 19 shows the result which was obtained by counting CGA-positive cells in GFP-positive cells after cell staining, and statistically processing the count by a Student t-test. * shows that there was a statistically significant difference between groups at P<0.01. It was revealed that CGA-positive cells are decreased in small cell lung cancer cultured strain H69 cells with an INI1-siRNA introduced therein, as compared with a group of No-treat, Control-siRNA.

Experimental Example 13, Result of Immunohistological Staining of Human Clinical Specimen of Small Cell Lung Cancer with Anti-INI1 Antibody To what extent INI1 is expressed in a small cell lung cancer exhibiting the neural differentiation potency was studied.

<Experimental Method>

1. In accordance with the Kumamoto University Ethical Codes, a formalin-fixed block of a human small cell lung cancer was obtained, and an experiment was performed.

Figure 20:
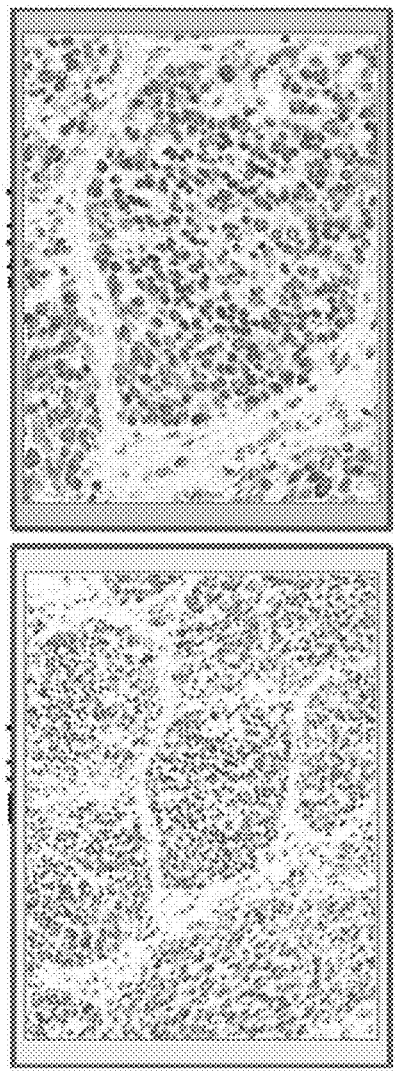
FIG. 20 is a view showing the result of INI1 immunostaining in a human pathological tissue.

2. A thin section of the block was prepared. Using an anti-INI1 rabbit polyclonal antibody (manufactured by Santa Cruz Biotechnology, No. sc-13055) as a primary antibody, and an anti-rabbit immunoglobulins-HRP antibody (manufactured by DAKO Co., Ltd.) as a secondary antibody, immunostaining was performed.
<Result>
1. The result of immunostaining is shown in FIG. 20. A left view is a view obtained by photographing at low power, and a right view is a view obtained by photographing at high power.
2. In a small cell lung cancer, brown staining exhibiting staining of INI1 strongly appeared. This revealed that expression of INI1 is high in a small cell lung cancer.

Experimental Example 14, Expression of Matrin-3, Phosphorylated Matrin-3 and INI1 in Neuroendocrine Tumor Neuroendocrine tumor exhibits the property of neural differentiation. Hence, involvement of the cancer stem cell controlling mechanism is strongly suggested. From this, for the purpose of investigating how the cancer stem cell control factor is expressed, study was performed.

Figure 22:
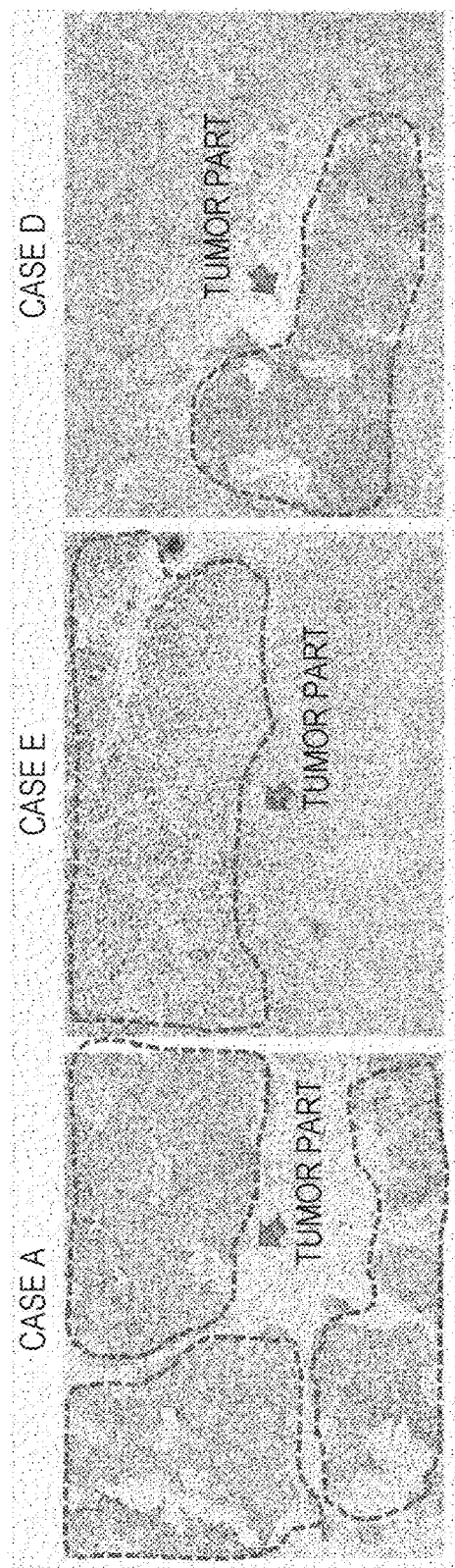
FIG. 22 is a view showing the result of immunostaining of phosphorylated Matrin-3 in Merkel's cell cancer, using a human pathological tissue section.
Figure 23:
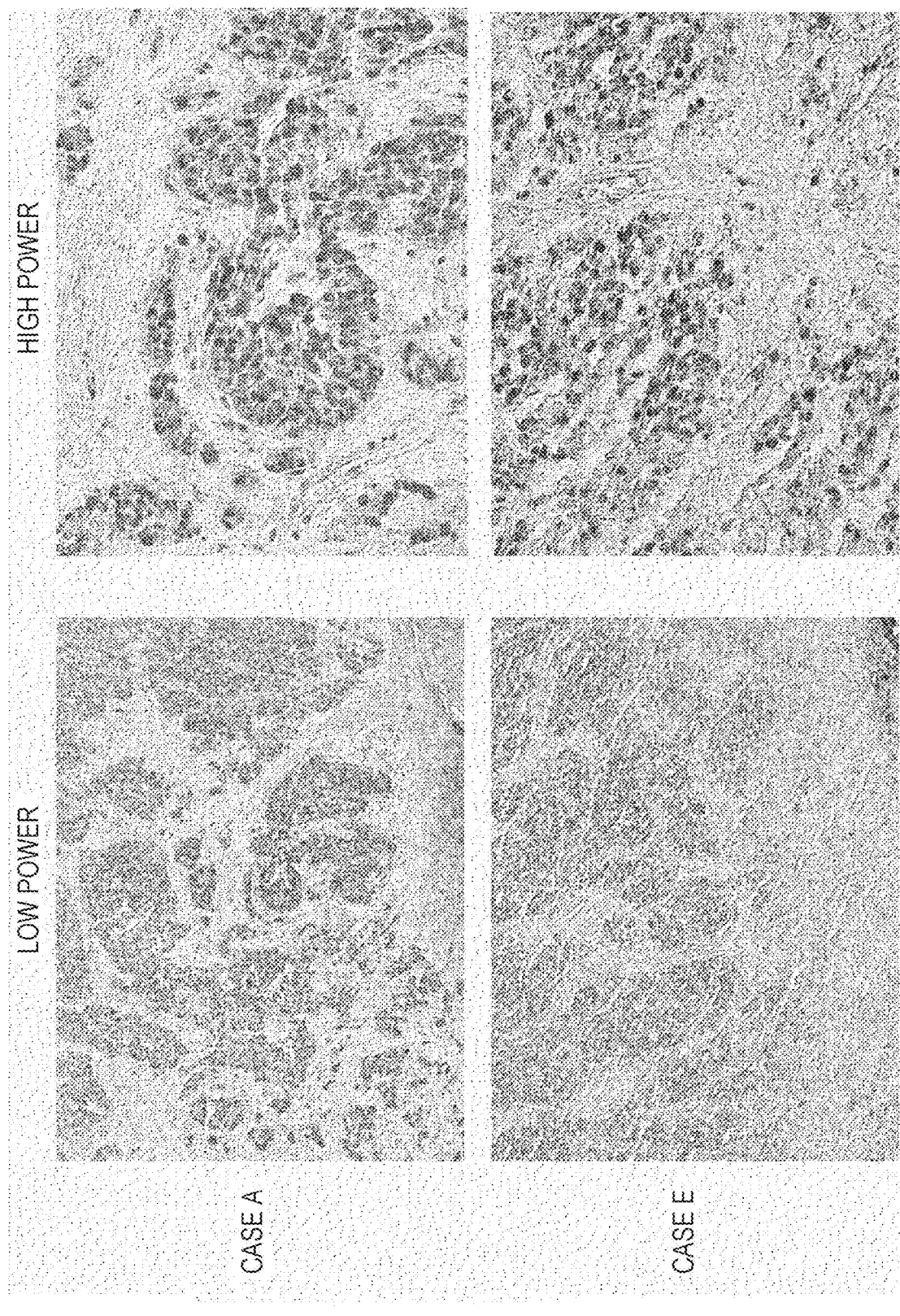
FIG. 23 is a view showing the result of immunostaining of INI1 in Merkel's cell cancer, using a human pathological tissue section.

As neuroendocrine tumor, stomach neuroendocrine tumor, rectum neuroendocrine tumor, and skin Merkel's cancer were targeted. Expression of Matrin-3 and INI1 in these tumors was investigated.
<Experimental Method>
1. In accordance with Experimental Example 3 and the like, an experiment was performed. That is, in accordance with the Kumamoto University Ethical Codes and the like, each human pathological tissue associated with neuroendocrine tumor was obtained, and an experiment was performed.
2. For immunostaining, staining was performed using the following antibodies, respectively.
(1) Matrin-3
Primary antibody: Anti-Matrin-3 mouse monoclonal antibody (manufactured by LifeSpan Biosciences, Inc., No. LS-C72171)
Secondary antibody: Anti-mouse immunoglobulins-HRP antibody (manufactured by DAKO Co., Ltd.)
(2) Phosphorylated Matrin-3
Primary antibody: Anti-phosphorylated Matrin-3 rabbit polyclonal antibody (manufactured by Bethyl Laboratories)
Secondary antibody: Polyclonal goat anti-rabbit immunoglobulins-HRP antibody (manufactured by DAKO Co., Ltd.)
(3) INI1
Primary antibody: Anti-INI1 rabbit polyclonal antibody (manufactured by Santa Cruz Biotechnology, No. sc-13055)
Secondary antibody: Anti-rabbit immunoglobulins-HRP antibody (manufactured by DAKO Co., Ltd.)
<Result>
1. FIG. 21 to FIG. 23 show the result of Merkel's cell cancer. Merkel's cell cancer is one kind of skin cancer. It is regarded that Merkel's cell cancer is developed from a Merkel's cell (basal layer) which is a neuroendocrine cell. It is known that a form and pathology thereof are very similar to those of small cell lung cancer.

(1) In Merkel's cell cancer, a tumor part is stained deeply with an anti-Matrin-3 antibody. From this, it was seen that expression of Matrin-3 is enhanced (FIG. 21, upper).

(2) In NF1 which is generated in the dermis, there is little staining with Matrin-3. From this, it was seen that there is no expression of Matrin-3 (FIG. 21, lower left).

(3) Also in Paget's disease which is generated in the epidermis, there is little staining with Matrin-3. From this, it was seen that there is no expression of Matrin-3 (FIG. 21, lower center).

(4) Also in SCC which is tumor of the epidermis, and in which tumor infiltrates up to the dermis, there is little staining with Matrin-3. From this, it was seen that there is no expression of Matrin-3 (FIG. 21, lower right).

(5) Additionally, in any of three different cases, a tumor part is stained deeply with an anti-phosphorylated Matrin-3 antibody. From this, it was seen that expression of phosphorylated Matrin-3 is enhanced (FIG. 22).

(6) Furthermore, in any of two different cases, a tumor part is stained with an anti-INI1 antibody. Thereby, it was seen that expression of INI1 is enhanced (FIG. 23).

Figure 24:
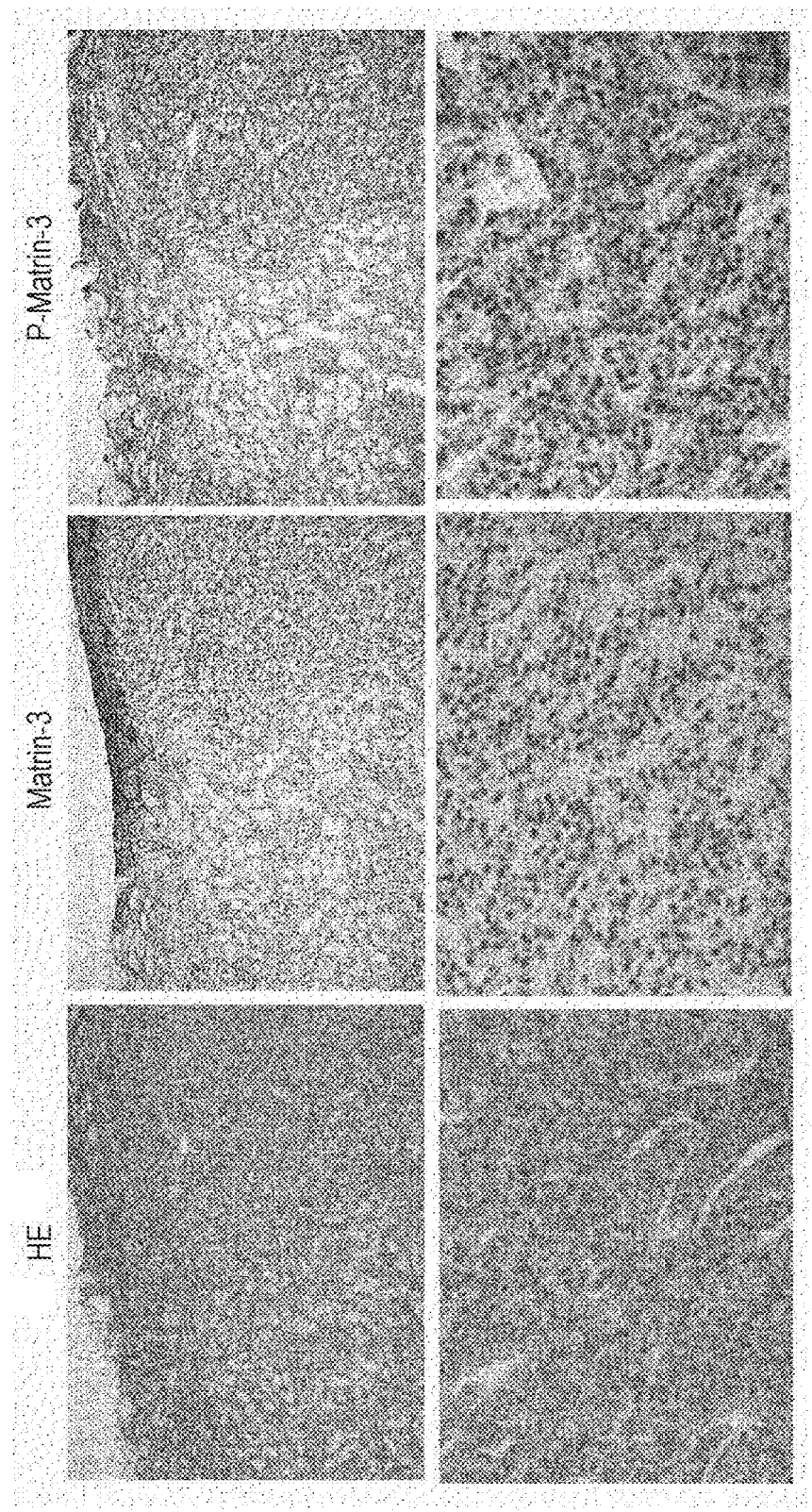
FIG. 24 is a view which was obtained by comparing the results of immunostaining of respective molecules of stomach neuroendocrine cancer exhibiting neural differentiation, using a human pathological tissue section.
Figure 25:
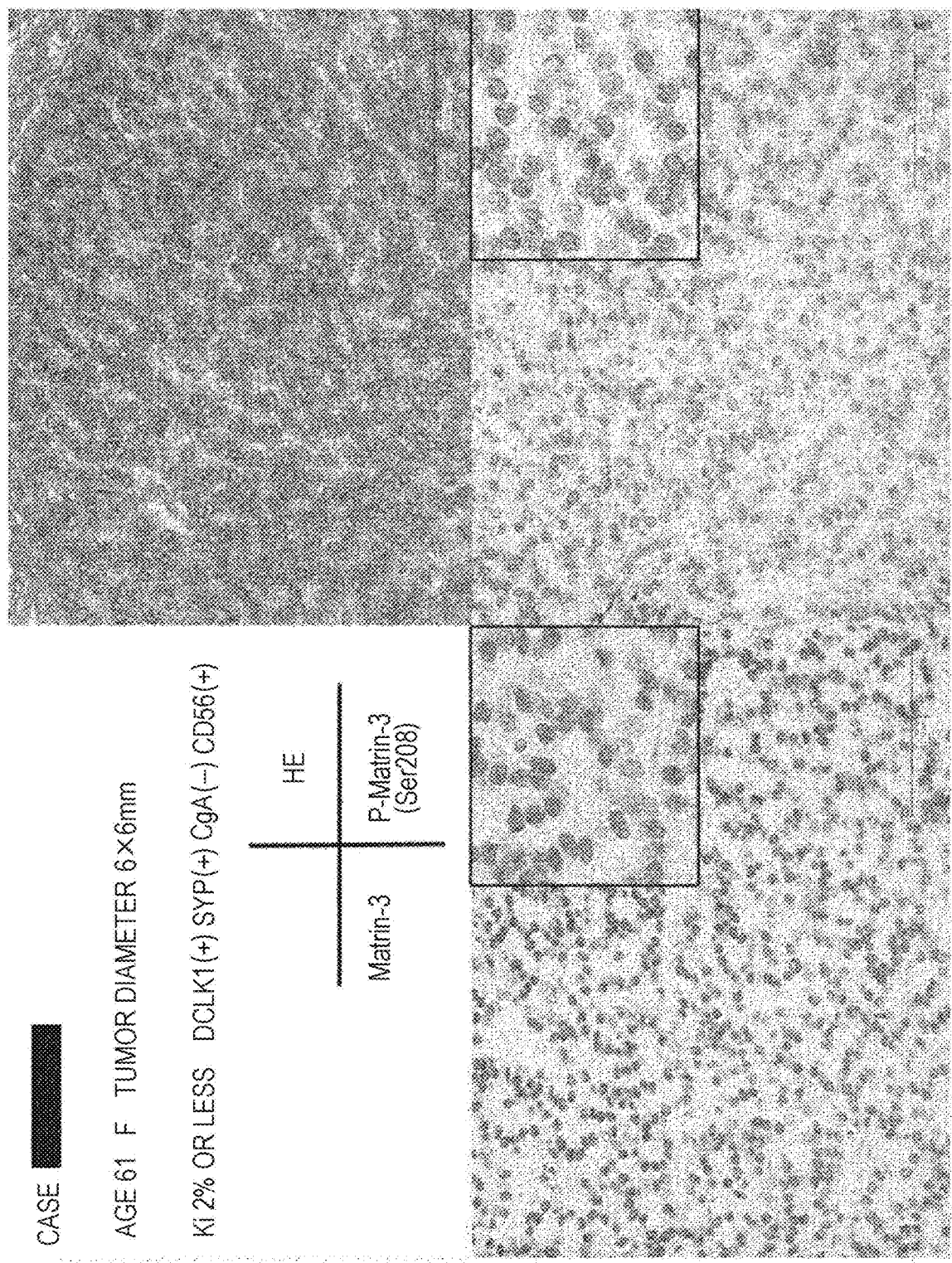
FIG. 25 is a view which was obtained by comparing the results of immunostaining of respective molecules of rectum neuroendocrine cancer exhibiting neural differentiation, using a human pathological tissue section.

(7) These showed that expression of Matrin-3 and phosphorylated Matrin-3 is increased only in Merkel's cell cancer exhibiting neural differentiation, in cancer in the skin. In addition, this result is the same result as the result in small cell lung cancer exhibiting neural differentiation (Experimental Example 3). 2. FIG. 24 and FIG. 25 show the result of neuroendocrine tumor (GI grade) of the stomach.

(1) In any of an anti-Matrin-3 antibody, and an anti-phosphorylated Matrin-3 antibody, a tumor part was stained deeply (FIG. 24).

(2) Additionally, also in the case different from that of FIG. 24, a tumor part was stained deeply with an anti-Matrin-3 antibody and an anti-phosphorylated Matrin-3 antibody (FIG. 25).

(3) From these, it was seen that expression of Matrin-3 and phosphorylated Matrin-3 is enhanced, in neuroendocrine tumor (GI grade) of the stomach.

Figure 26:
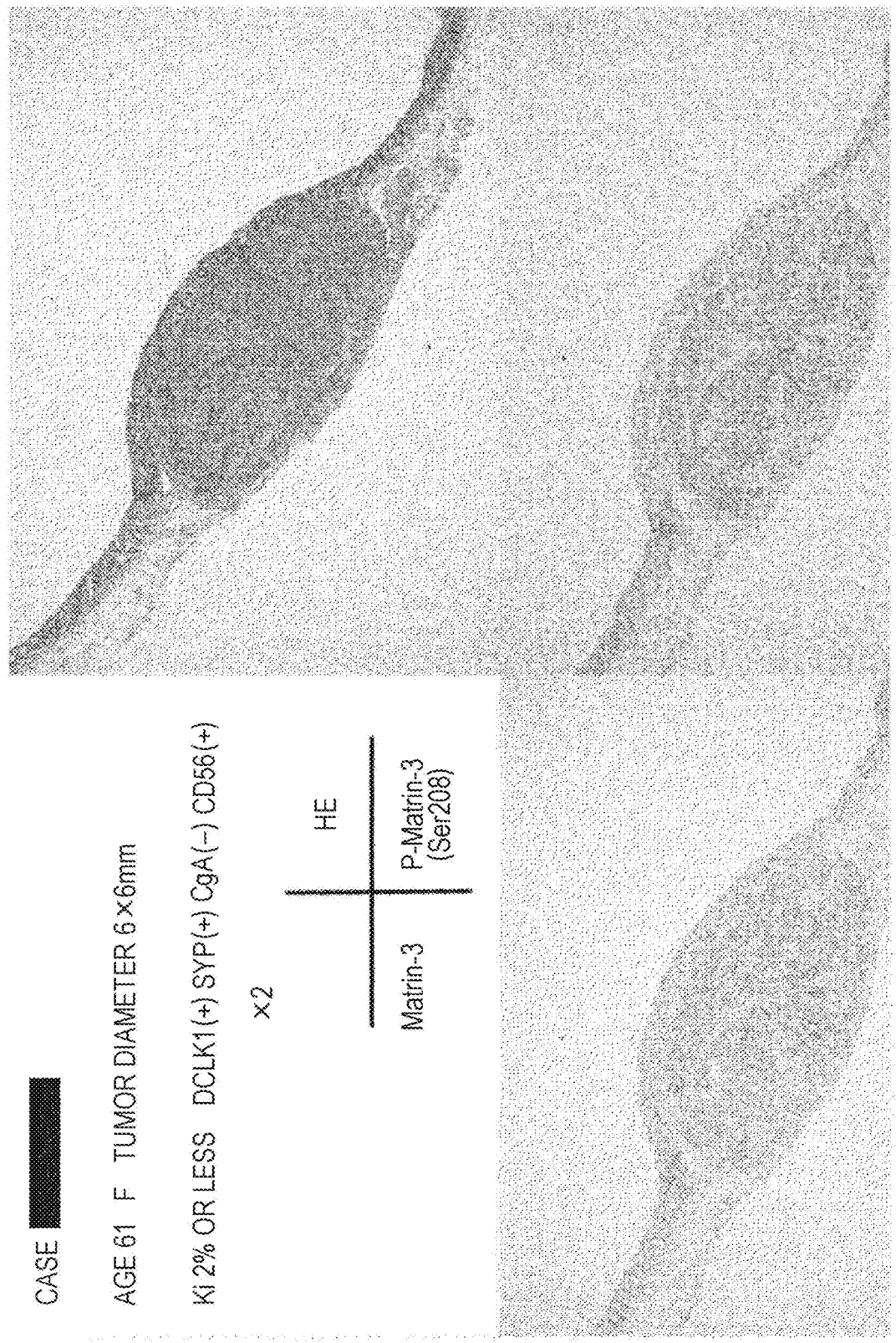
FIG. 26 is a view which was obtained by comparing the results of immunostaining of respective molecules of rectum neuroendocrine cancer exhibiting neural differentiation, using a human pathological tissue section.

3. FIG. 26 shows the result of neuroendocrine tumor (GI grade) of the rectum. In any of an anti-Matrin-3 antibody and an anti-phosphorylated Matrin-3 antibody, a tumor part is stained deeply. From this, it was seen that expression of Matrin-3 and phosphorylated Matrin-3 is enhanced.

4. From these results, expression of Matrin-3, phosphorylated Matrin-3, and INI1 is increased in neuroendocrine tumor exhibiting neural differentiation. This showed that the neuroendocrine tumor has the cancer cell controlling mechanism.

The invention claimed is:

1. A method for suppressing the proliferation of small cell lung cancer cells, comprising introducing a siRNA or shRNA to the small cell lung cancer cells to suppress expression of a stem cell control factor, wherein the stem cell control factor is Matrin-3 or INI1, and wherein
the siRNA to Matrin-3 has the sequences of SEQ ID NO:1 and SEQ ID NO:2; SEQ ID NO:3 and SEQ ID NO:4; or SEQ ID NO: 5 and SEQ ID NO:6;
the shRNA to Matrin-3 has a sequence of any one of SEQ ID NO: 7 to 10, and
the siRNA to INI1 has the sequences of SEQ ID NO: 11 and SEQ ID NO: 12; SEQ ID NO: 13 and SEQ ID NO: 14; or SEQ ID NO: 15 and SEQ ID NO: 16.

2. A method for suppressing the neural differentiation of small cell lung cancer cells, comprising introducing a siRNA to INI1 to the small cell lung cancer cells to suppress expression of INI1, wherein the siRNA to INI1 has the sequences of SEQ ID NO: 11 and SEQ ID NO: 12; SEQ ID NO: 13 and SEQ ID NO: 14; or SEQ ID NO: 15 and SEQ ID NO: 16.

* * * * *